US011426385B2

(12) United States Patent
Hammock et al.

(10) Patent No.: US 11,426,385 B2
(45) Date of Patent: Aug. 30, 2022

(54) METHODS OF IMPROVING CANCER CHEMOTHERAPY

(71) Applicants: THE REGENTS OF THE UNIVERSITY OF CALIFORNIA, Oakland, CA (US); United States as represented by the Department of Veterans Affairs, Washington, DC (US)

(72) Inventors: Bruce D. Hammock, Davis, CA (US); Sung Hee Hwang, Woodland, CA (US); Ralph W. de Vere White, Sacramento, CA (US); Chong-xian Pan, Sacramento, CA (US); Hongyong Zhang, Sacramento, CA (US); Paul Henderson, Sacramento, CA (US); Ai-Hong Ma, Sacramento, CA (US); Maike Zimmermann, Sacramento, CA (US); Fuli Wang, Xi'an (CN)

(73) Assignees: THE REGENTS OF THE UNIVERSITY OF CALIFORNIA, Oakland, CA (US); United States as represented by the Department of Veterans Affairs, Washington, DC (US)

( * ) Notice: Subject to any disclaimer, the term of this patent is extended or adjusted under 35 U.S.C. 154(b) by 143 days.

(21) Appl. No.: 16/641,430

(22) PCT Filed: Aug. 14, 2018

(86) PCT No.: PCT/US2018/046649
§ 371 (c)(1),
(2) Date: Feb. 24, 2020

(87) PCT Pub. No.: WO2019/040319
PCT Pub. Date: Feb. 28, 2019

(65) Prior Publication Data
US 2020/0197368 A1 Jun. 25, 2020

Related U.S. Application Data

(60) Provisional application No. 62/549,958, filed on Aug. 25, 2017.

(51) Int. Cl.
| | |
|---|---|
| *A61K 31/415* | (2006.01) |
| *A61P 35/00* | (2006.01) |
| *A61K 33/243* | (2019.01) |
| *A61K 31/7068* | (2006.01) |
| *A61K 45/06* | (2006.01) |

(52) U.S. Cl.
CPC ........ *A61K 31/415* (2013.01); *A61K 31/7068* (2013.01); *A61K 33/243* (2019.01); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 9,096,532 | B2 | 8/2015 | Hammock et al. |
| 2014/0038923 | A1 | 2/2014 | Hammock et al. |

FOREIGN PATENT DOCUMENTS

| | | |
|---|---|---|
| WO | 2000038730 A2 | 7/2000 |
| WO | 2012082647 A2 | 6/2012 |

OTHER PUBLICATIONS

International Search Report of PCT/US2018/046649 dated Oct. 24, 2018.
Written Opinion of the International Searching Authority for PCT/US2018/046649 dated Oct. 24, 2018.
Zhang et al., "Dual inhibition of cyclooxygenase-2 and soluble epoxide hydrolase synergistically suppresses primary tumor growth and metastasis", Proceedings of the National Academy of Sciences of the United States of America, Jul. 29, 2014, vol. 111, No. 30, pp. 11127-11132.
Borghaei et al., "Nivolumab versus Docetaxel in Advanced Nonsquamous Non-Small-Cell Lung Cancer", The New England Journal of Medicine, Oct. 22, 2015, 373(17):1627-39.
Burchardt et al., "Favorable combination effects of the leukotriene synthesis inhibitor BAY X 1005 and dexamethasone on edema formation in the arachidonic acid-induced mouse ear inflammation test", Prostaglandins Leukotrienes and Essential Fatty Acids, 1999, 60(1):5-11.
Chou, "Drug Combination Studies and Their Synergy Quantification Using the Chou-Talalay Method", Cancer Research, 2010, 70:440-6.
Chou, "Theoretical basis, experimental design, and computerized simulation of synergism and antagonism in drug combination studies", Pharmacological Reviews, 2006, 58:621-81.
Englehart et al., "Anti-inflammatory, analgesic, antipyretic and related properties of meloxicam, a new non-steroidal anti-inflammatory agent with favourable gastrointestinal tolerance", Inflammatory Res, 1995, 44:422-33.
Ghosh et al., "COX-2 as a target for cancer chemotherapy", Pharmacological Reports, 2010, 62:233-44.
Goswami et al., "Anti-Ulcer Efficacy of Soluble Epoxide Hydrolase Inhibitor TPPU on Diclofenac-Induced Intestinal Ulcers", The Journal of Pharmacology and Experimental Therapeutics, 2016, 357:529-36.

(Continued)

*Primary Examiner* — Brian J Davis
(74) *Attorney, Agent, or Firm* — Mintz, Levin Cohn, Ferris, Glovsky and Popeo, P.C.

(57) ABSTRACT

Provided are methods and compositions for prolonging survival and/or reducing or inhibiting tumor growth in a cancer subject receiving a regimen of one or more chemotherapeutic agents, an inhibitor of soluble epoxide hydrolase (sEHi) and a non-steroidal anti-inflammatory drug (NSAID) that inhibits one or more enzymes selected from the group consisting of cyclo-oxygenase ("COX")-1, COX-2, and 5-lipoxygenase ("5-LOX"). The methods and compositions decrease toxicity and/or adverse side effects in subjects receiving a regimen of one or more chemotherapeutic agents.

21 Claims, 19 Drawing Sheets

(56) References Cited

OTHER PUBLICATIONS

Gridelli et al., "Factorial phase III randomised trial of rofecoxib and prolonged constant infusion of gemcitabine in advanced non-small-cell lung cancer: the GEmcitabine-COxib in NSCLC (GECO) study", The Lancet Oncology, 2007, 8:500-12.
Grivas et al., "Evaluation of the Antitumor Activity of Dacomitinib in Models of Human Bladder Cancer", Molecular Medicine, 2013, 19:367-76.
Groen et al., "Randomized, Placebo-Controlled Phase III Study of Docetaxel Plus Carboplatin with Celecoxib and Cyclooxygenase-2 Expression as a Biomarker for Patients With Advanced Non-Small-Cell Lung Cancer: The NVALT-4 Study", Journal of Clinical Oncology, Nov. 10, 2011, 29:4320-4326.
Hakonarson et al., "Effects of a 5-Lipoxygenase-Activating Protein Inhibitor on Biomarkers Associated With Risk of Myocardial Infarction", JAMA, May 11, 2005, 293(18):2245-2256.
Hatzelmann et al., "Mode of Action of th New Selective Leukotriene Synthesis Inhibitor BAY X 1005 {(R)-2-[4-(Quinolin-2-YL-Methoxy)Phenyl]-2-Cyclopentyl Acetic Acid} and Structurally Related Compounds", Biochemical Pharmacology, 1993, 45(1):101-11.
Henderson et al., "A microdosing approach for characterizing formation and repair of carboplatin-DNA monoadducts and chemoresistance", International Journal of Cancer, 2011, 129(6):1425-34.
Henderson et al., "Human microdosing for the prediction of subject response", Bioanalysis, 2010, 2(3):373-6.
Ho et al., "Cisplatin versus carboplatin: comparative review of therapeutic management in solid malignancies",Critical Reviews in Oncology/Hematology, 2016, 102:37-46.
Hwang et al., "Orally Bioavailable Potent Soluble Epoxide Hydrolase Inhibitors", Journal of Med Chem, Aug. 9, 2007, 50(16):3825-40.
Hwang et al, "Synthesis and Structure-Activity Relationship Studies of Urea-Containing Pyrazoles as Dual Inhibitors of Cyclooxygenase-2 and Soluble Epoxide Hydrolase", Journal of Med Chem, Apr. 28, 2011, 54(8):3037-50.
Inceoglu et al., "Soluble epoxide hydrolase and epoxyeicosatrienoic acids modulate two distinct analgesic pathways", Proceedings of the National Academy of Sciences of the United States of America, Dec. 2, 2008, vol. 105, No. 28, pp. 18901-18906.
Julemont et al., "Recent developments in 5lipoxygenase inhibitors", Expert Opinion on Therapeutic Patents, 2003, 13(1):1-13.
Kamat et al., "Bladder cancer", Lancet, 2016, 388:2796-2810.
Kodani et al., "The 2014 Bernard B. Brodie Award Lecture-Epoxide Hydrolases: Drug Metabolism to Therapeutics for Chronic Pain", Drug Metabolism and Disposition, May 2015, 43:788-802.
Kurtova et al., "Blocking PGE2-induced tumour repopulation abrogates bladder cancer chemoresistance", Nature, Jan. 8, 2015, 517(7533):209-13.
Lazaar et al., "Pharmacokinetics, pharmacodynamics and adverse event profile of GSK2256294, a novel soluble epoxide hydrolase inhibitor", British Journal of Clinical Pharmacology, Dec. 1, 2015, 81:5, pp. 971-979.
Liu et al., "Inhibition of soluble epoxide hydrolase enhances the anti-inflammatory effects of aspirin and 5-lipoxygenase activation protein inhibitor in a murine model", Biochem Pharmacol, 2010, 79(6):880-887.
Mancini et al., "Cellular Oxygenation of 12-Hydroxyeicosatetraenoic Acid and 15-Hydrocyeicosatetraenoic Acid by 5-Lipoxygenase Is Stimulated by 5-Lipoxygenase-activating Protein", The Journal of Biological Chemistry, 1998, vol. 273, No. 49, pp. 32842-32847.
Morisseau et al., "Impact of Soluble Epoxide Hydrolase and Epoxyeicosanoids on Human Health", Annual Review of Pharmacology and Toxicology, 2013, 53:37-58.
Morisseau et al., "Potent urea and carbamate inhibitors of soluble epoxide hydrolases", Proc. Natl. Acad. Sci. USA, 1999, 96:8849-8854.
Ognibene et al., "A High-Throughput Method for the Conversion of CO2 Obtained from Biochemical Samples to Graphite in Septa-Sealed Vials for Quantification of 14C via Accelerator Mass Spectrometry", Analytical Chemistry, 2003, 75:2192-2196.
Pan et al., "A phase II Trial of Irinotecan, 5-Fluorouracil and Leucovorin Combined with Celecoxib and Glutamine as First-Line Therapy for Advanced Colorectal Cancer", Oncology, 2005, 69:63-70.
Pan et al., "Development and Characterization of Bladder Cancer Patient-Derived Xenografts for Molecularly Guided Targeted Therapy", PloS ONE, 2015, 10(8):e0134346.
Powles et al., "MPDL3280A (anti-PD-L1) treatment leads to clinical activity in metastatic bladder cancer", Nature, 2014, 515:558-562.
Schmelzer et al., "Enhancement of antinociception by coadministration of nonsteroidal anti-inflammatory drugs and soluble epoxide hydrolase inhibitors", Proceedings of the National Academy of Sciences of the United States of America, Sep. 12, 2006, vol. 103, No. 37, pp. 13646-13651.
Schmelzer et al., "Soluble epoxide hydrolase is a therapeutic target for acute inflammation", Proceedings of the National Academy of Sciences of the United States of America, Jul. 12, 2005, vol. 102, No. 28, pp. 9772-9777.
Sebaugh, J. L., "Guidelines for accurate EC50/IC50 estimation", Pharmaceutical Statistics, 2011, 10:128-34.
Shen et al., "Discovery of Inhibitors of Soluble Epoxide Hydrolase: A Target with Multiple Potential Therapeutic Indications", Journal of Med Chem, Mar. 8, 2012, 55(5):1789-1808.
Spector et al., "Epoxyeicosatrienoic acids (EETs): metabolism and biochemical function", Progress in Lipid Research, 2004, 43:55-90.
Spector et al., "Action of epoxyeicosatrienoic acids on cellular function", American Journal of Physiology Cell Physiology, 2007, 292:C996-1012.
Thalji et al., "Discovery of 1-(1,3,5-triazin-2-yl)piperidine-4-carboxamides as inhibitors of soluble epoxide hydrolase", Bioorganic & Medicinal Chemistry Letters, 2013, 23:3584-3588.
Titos et al., "Inhibition of 5-lipoxygenase induces cell growth arrest and apoptosis in rat Kupffer cells: implications for liver fibrosis", The FASEB Journal, Jul. 3, 2003, 17:1745-1747.
Wagner et al., "Soluble Epoxide Hydrolase Inhibition, Epoxygenated Fatty Acids and Nociception", Prostaglandins Other Lipid Mediators, Nov. 2011, 96(1-4):76-83.
Wang et al., "Molecular Dissection of Induced Platinum Resistance through Functional and Gene Expression Analysis in a Cell Culture Model of Bladder Cancer", PloS ONE, Jan. 22, 2016, 11:e0146256.
Xu et al., "COX-2 Inhibition Potentiates Antiangiogenic Cancer Therapy and Prevents Metastasis in Preclinical Models", Science Translational Medicine, Jun. 25, 2014, 6(242):242ra84.
Zhang et al., "Dual inhibition of cyclooxygenase-2 and soluble epoxide hydrolase synergistically suppresses primary tumor growth and metastasis", Proceedings of the National Academy of Sciences of the United States of America, Jul. 29, 2014, vol. 111, No. 20, pp. 11127-11132.
Zimmermann et al., "Microdose-Induced Drug-DNA Adducts as Biomarkers of Chemotherapy Resistance in Humans and Mice", Mol Cancer Ther., Feb. 2017, 16(2):376-387.

Previously Disclosed Compound

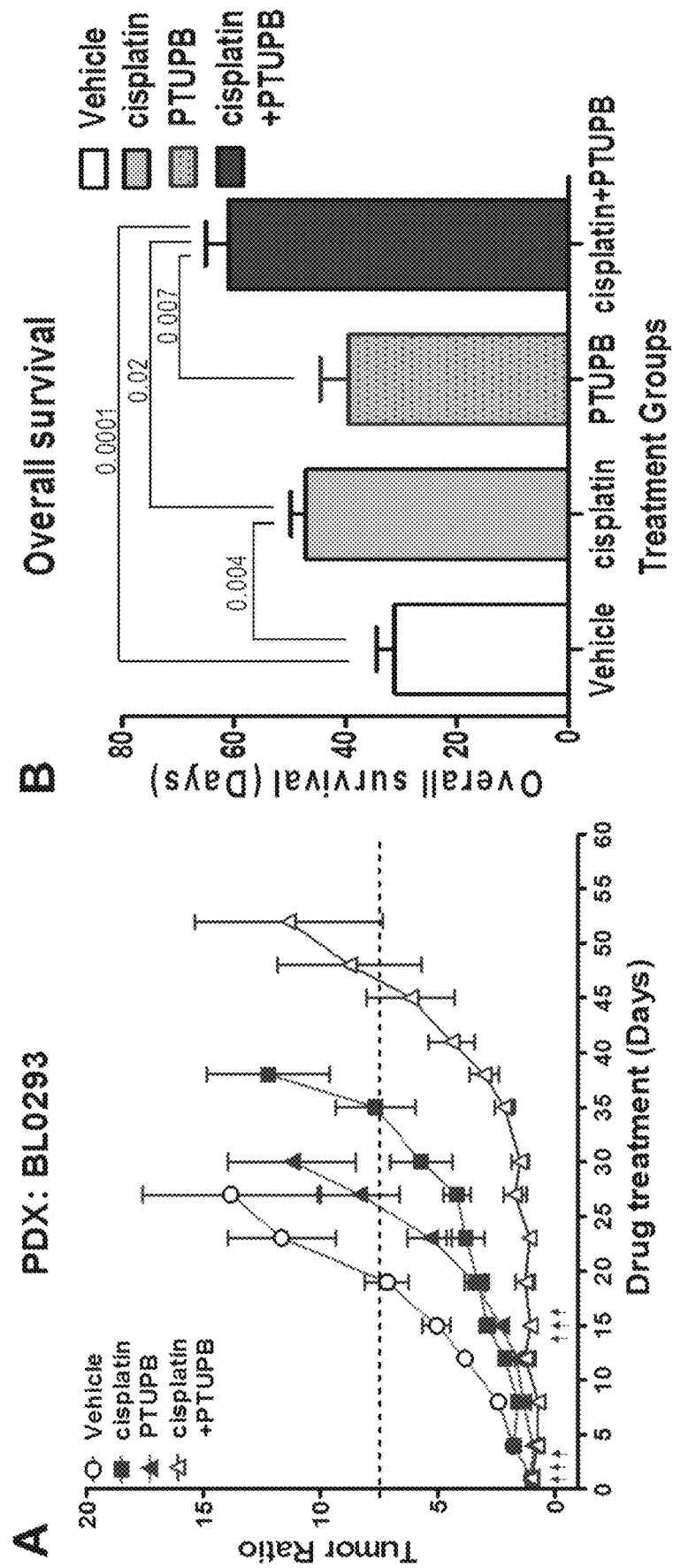
Fig. 2A-B

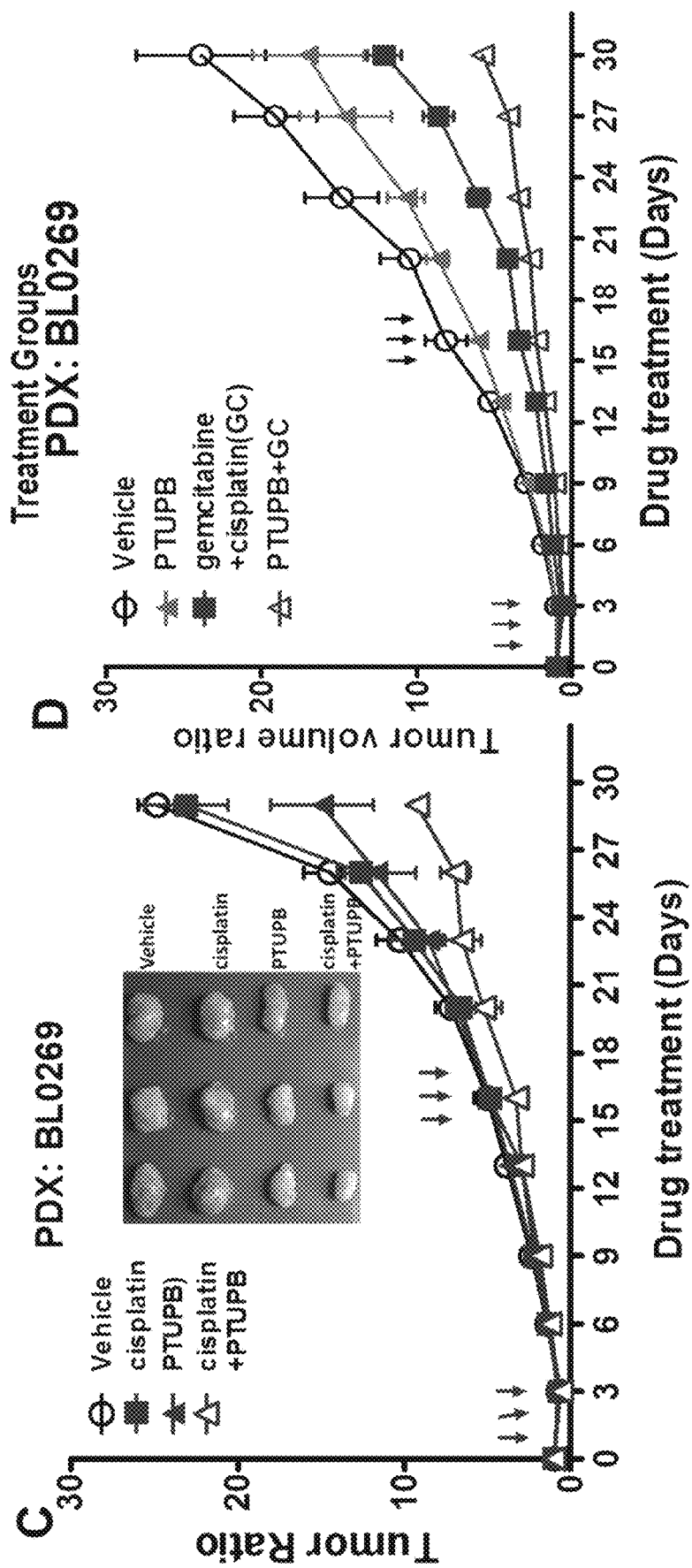
Fig. 2C-D

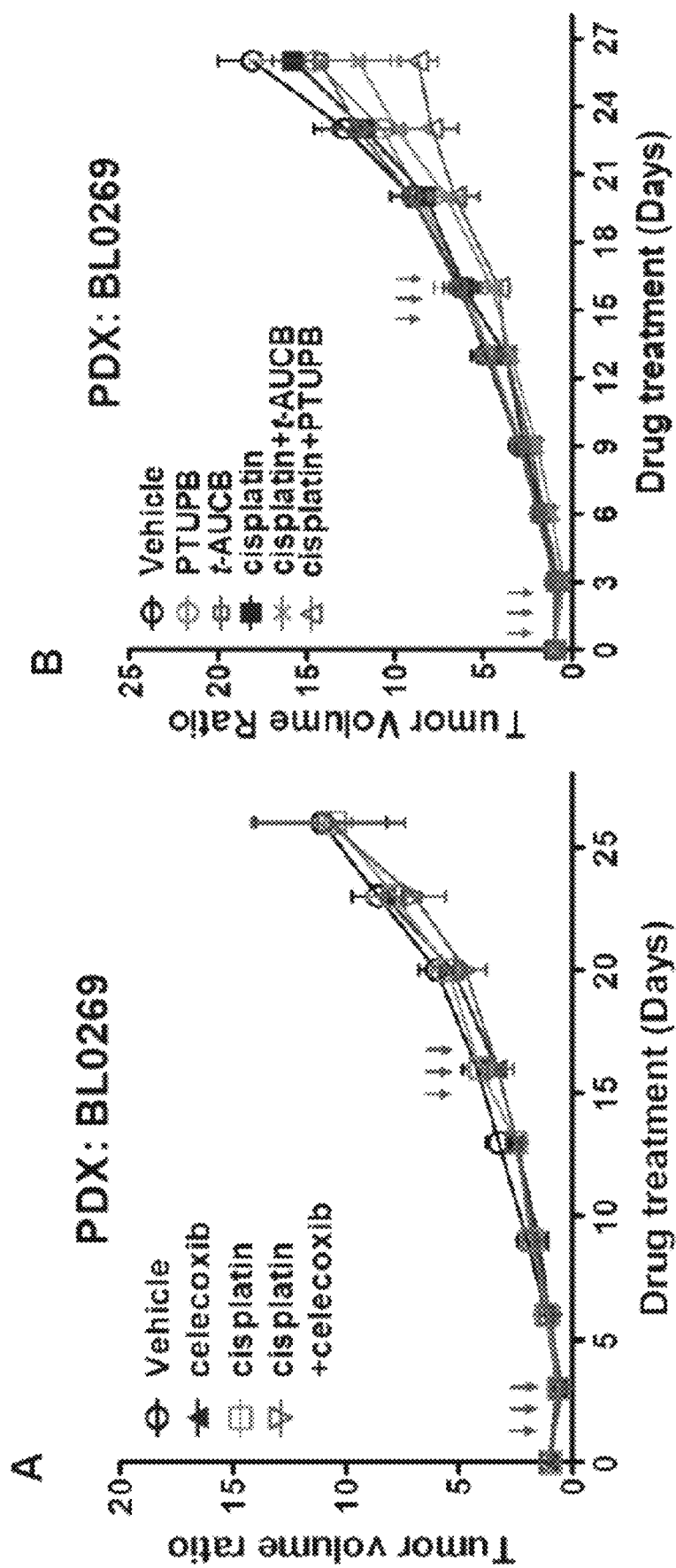
Fig. 3A-B

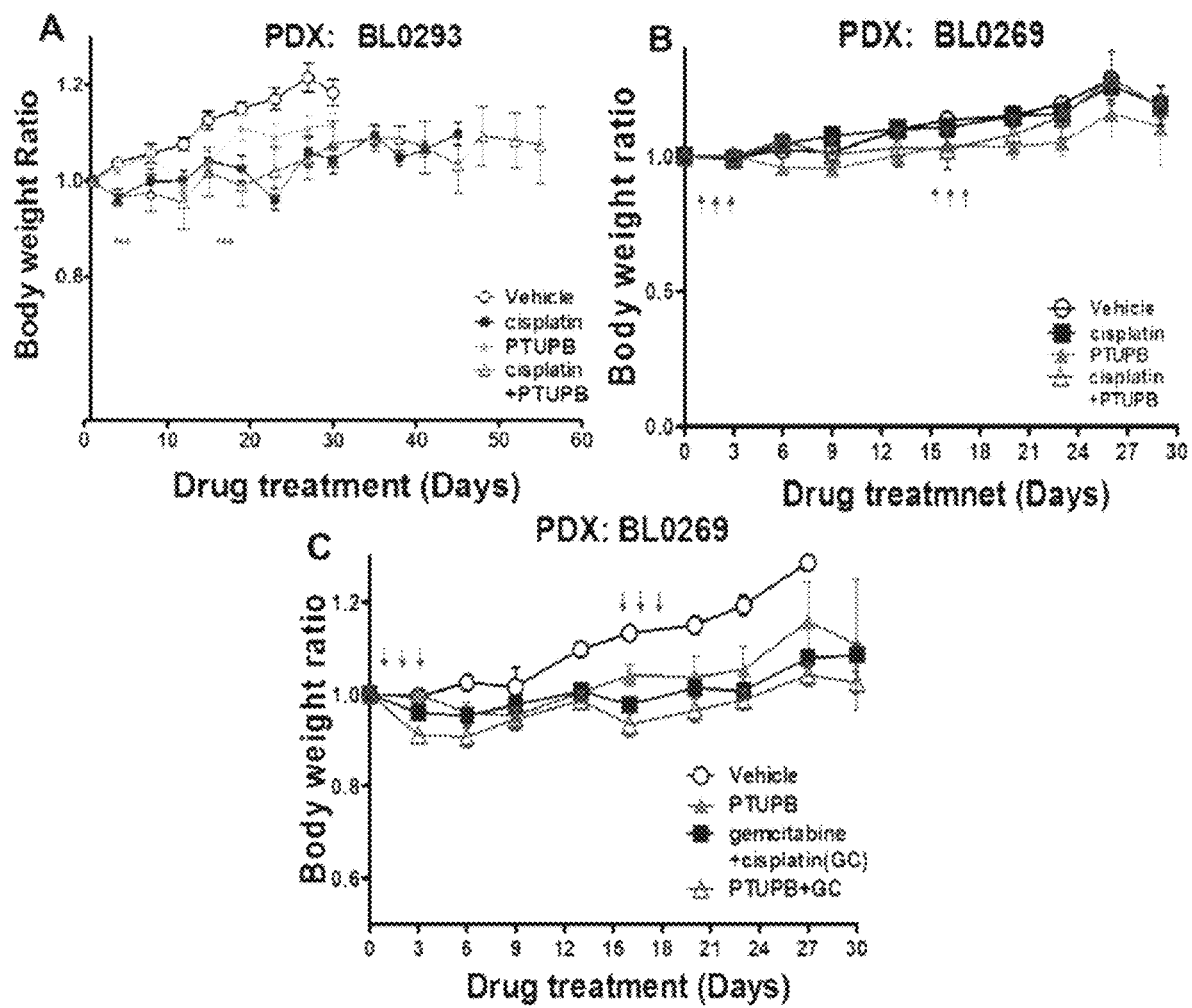
Fig. 4A-C

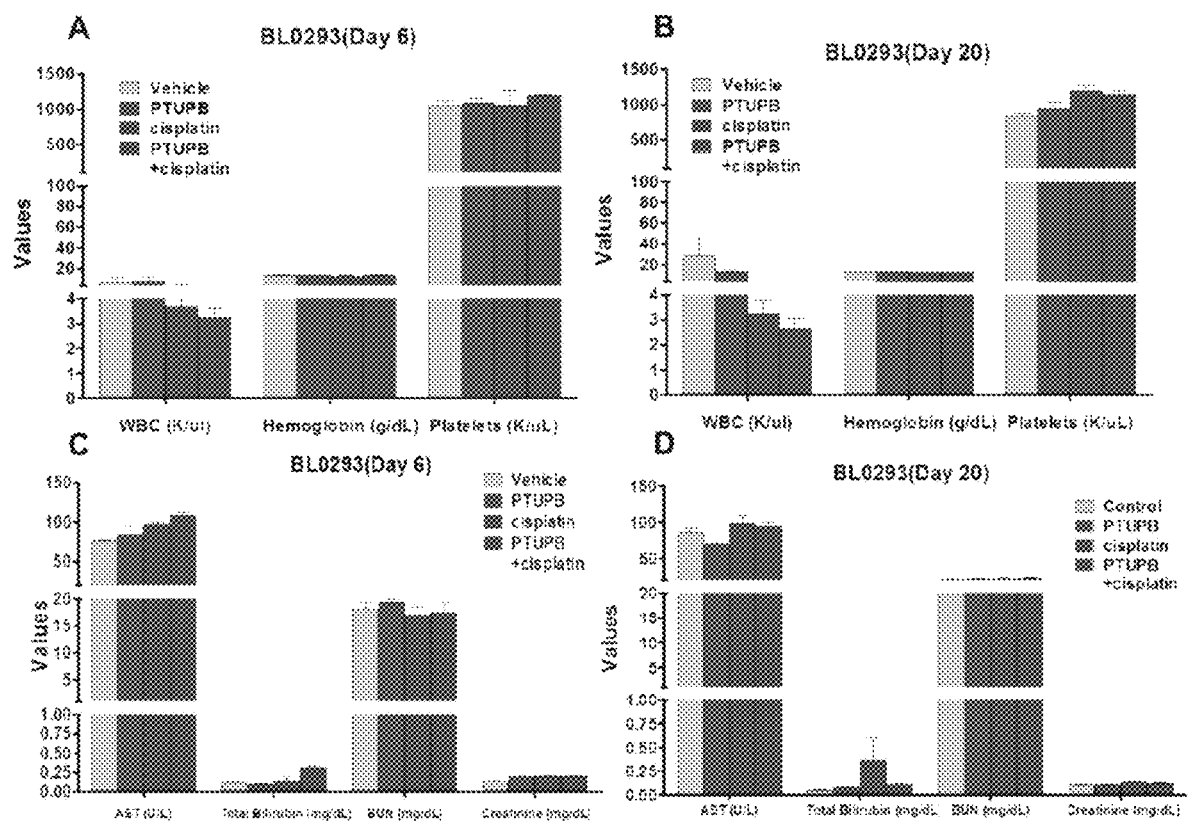
Fig. 5A-D

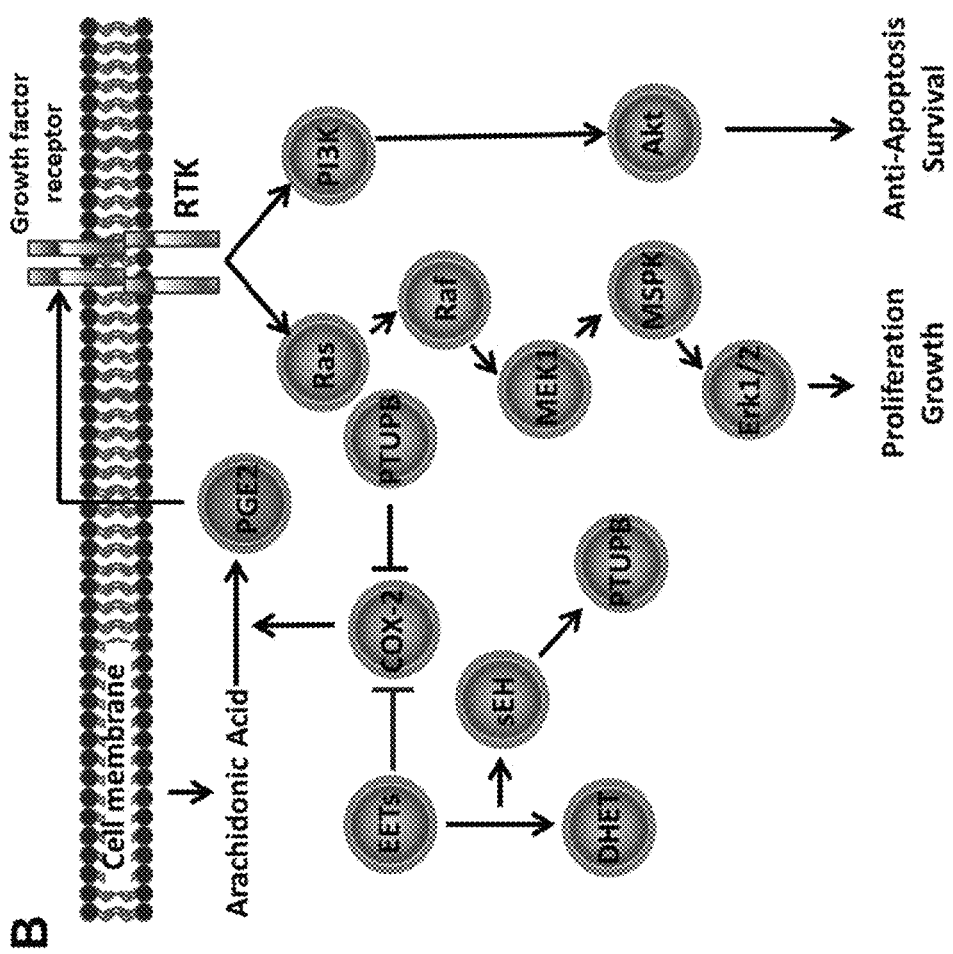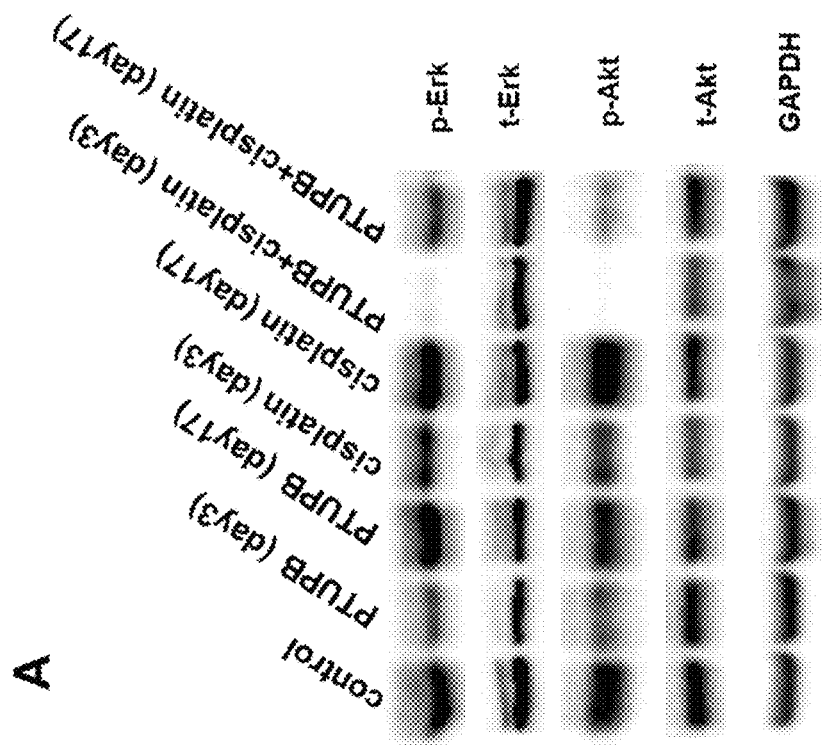
Fig. 9A-B

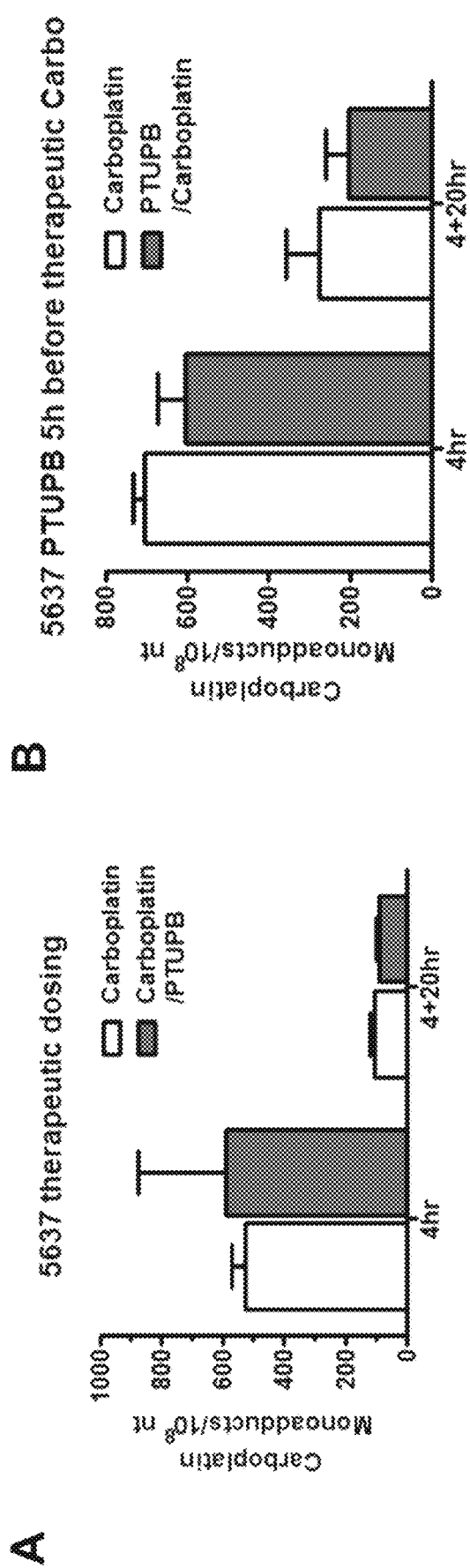
Fig. 10A-B

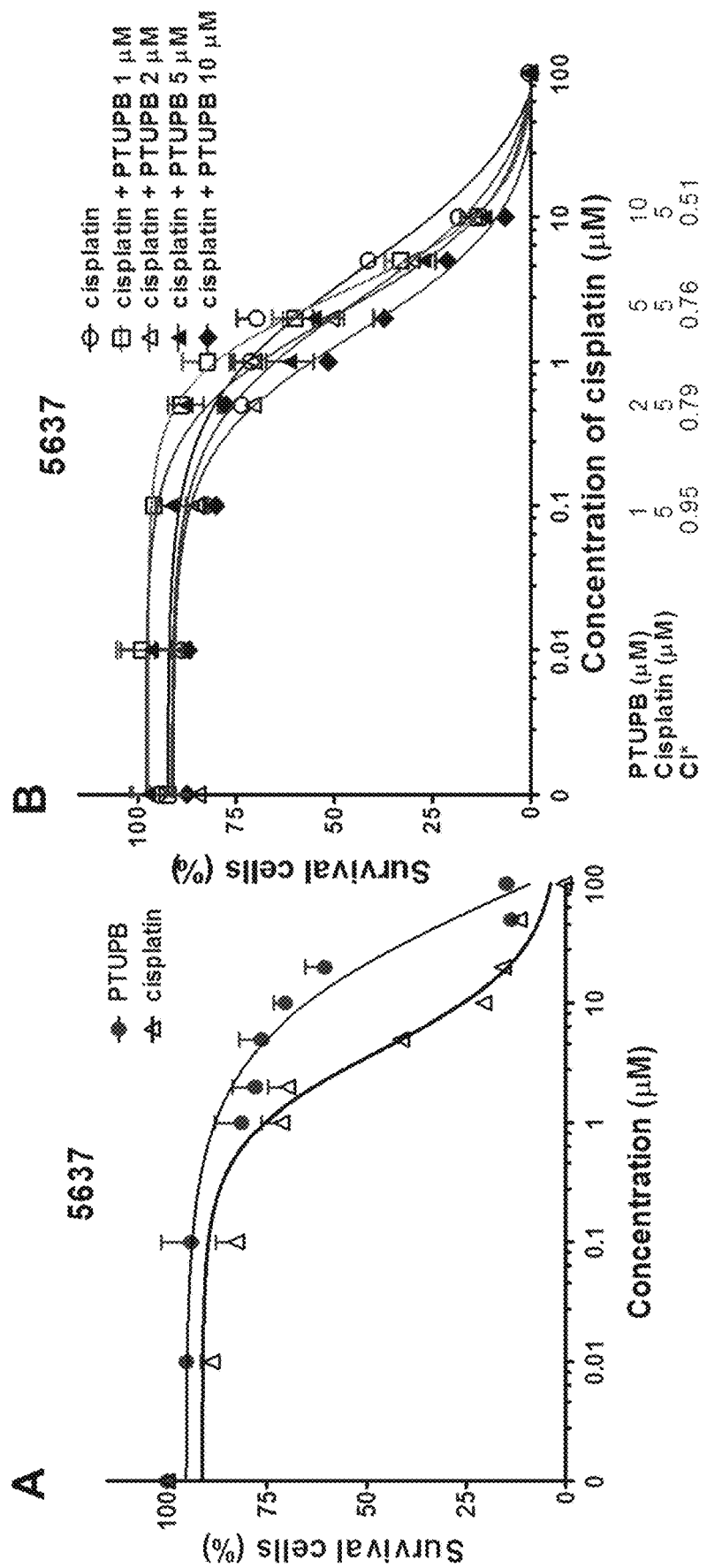
Fig. 11A-B

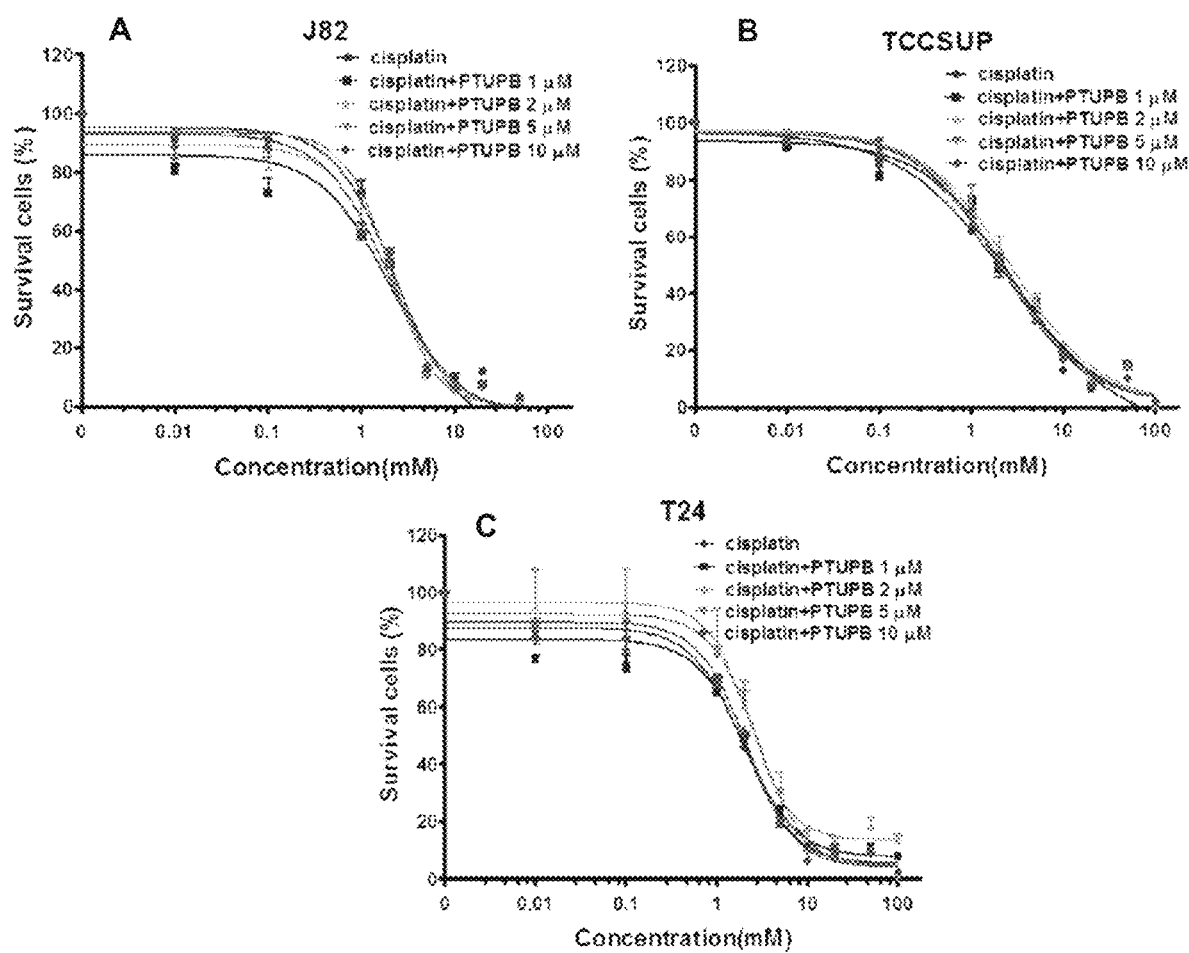
Fig. 12A-C

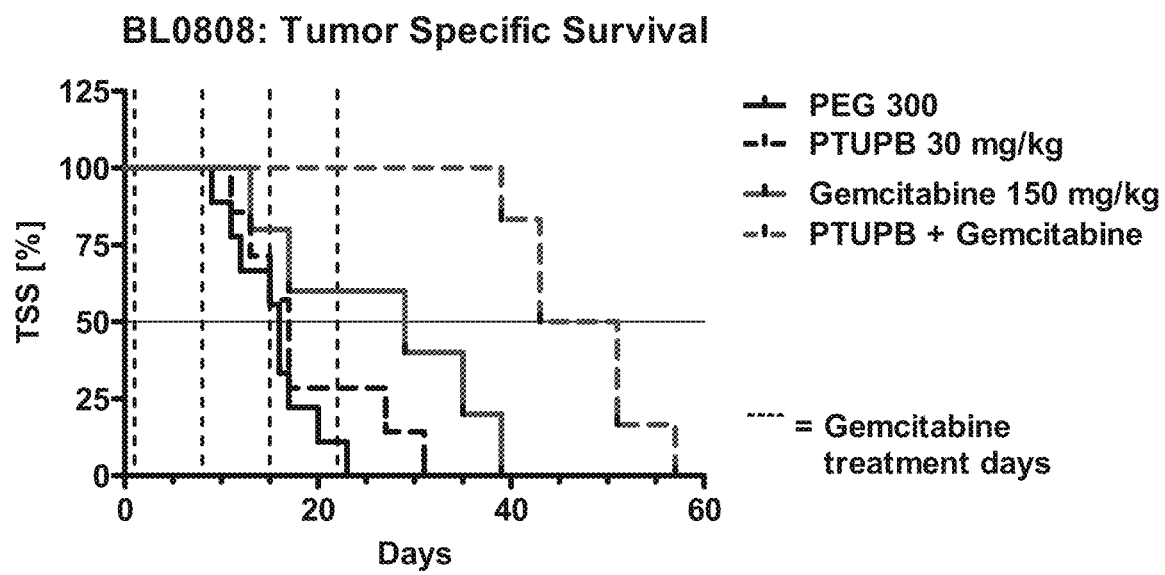
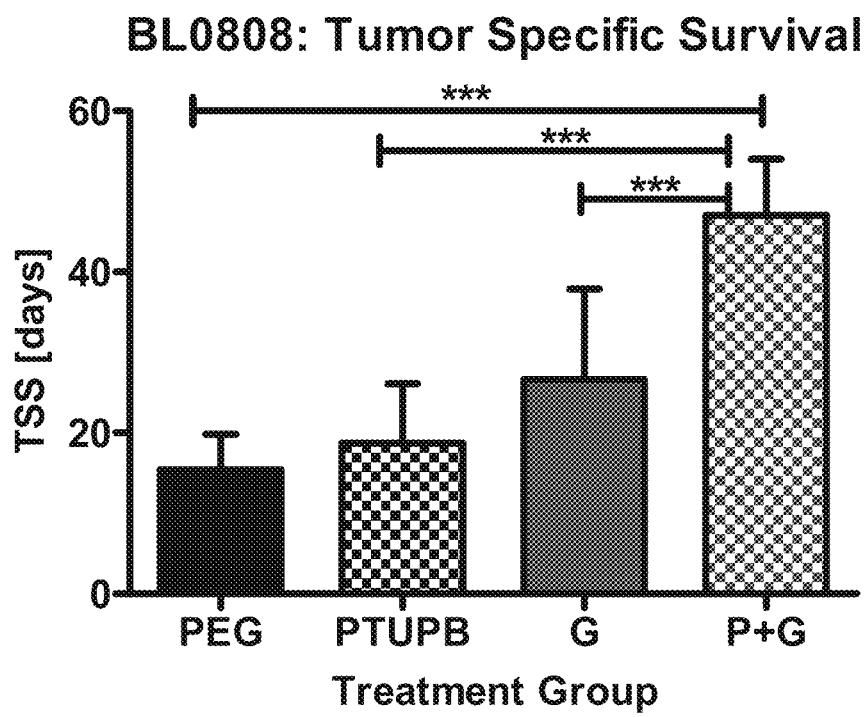
Fig. 14B

METHODS OF IMPROVING CANCER CHEMOTHERAPY

CROSS-REFERENCE TO RELATED APPLICATIONS

This application is the U.S. national phase under 35 U.S.C. 371 of International Application No. PCT/US2018/046649, filed Aug. 14, 2018, which claims the benefit under 35 U.S.C. § 119(e) of U.S. Provisional Application No. 62/549,958, filed on Aug. 25, 2017, which are hereby incorporated herein by reference in their entireties for all purposes.

STATEMENT OF GOVERNMENTAL SUPPORT

This invention was made with government support under Grant Nos. 2P30CA0933730, R01E5002710, P42ES04699, HHSN261201200048C, R01DK103616 and U54NS079202, all awarded by the National Institutes of Health, and I01BX001784, awarded by the U.S. Department of Veterans Affairs. The government has certain rights in the invention

BACKGROUND

Chemotherapy remains a mainstream treatment for many types of cancers. Although effective at killing tumor cells, chemotherapy has significant limitations. Chemotherapeutic agents are toxic. As such, the dose level and dosing range for chemotherapeutic agents are limited by toxicity. The duration of treatment with chemotherapeutic agents is also confined based on accumulated toxicity and other quality of life issues. For example, cisplatin is the most commonly used chemotherapeutic agent in cancer treatment. However, it is only moderately effective in most cancer types and is highly toxic (1). Cisplatin-based first-line combination therapy is associated with a response rate of approximately 50% for metastatic bladder cancer, and induces complete remission in less than 40% at the neoadjuvant setting for this disease (2). Yet there are limitations to the dosing and length of treatment with this agent. Chemotherapeutic agents can be used singly and in combination. Because of the accumulative toxicity when more than one agent is combined, these combinations can be further limited in their dosing range and treatment duration.

SUMMARY

Provided herein are compositions and methods to improve the utility and effectiveness of chemotherapy treatments by providing combinations of anti-cancer agents that can improve the effectiveess of chemotherapy without adding to or increasing toxicity and other unwanted side effects. Provided herein are anti-cancer agents for use in combination with one or more chemotherapeutic agents for treatment of cancer and methods of treatment using combinations of anti-cancer agent(s) and chemotherapeutic agent(s).

In some embodiments of the compositions and methods herein prolong survival of the treated subject. In some embodiments, the compositions and methods herein reduce or inhibit tumor growth in a subject receiving the regimen. In some embodiments herein, the methods and compositions provide for a longer duration or increased cycles of treatment with one or more chemotherapeutic agents. In some embodiments, the methods and compositions provide for an increase in the effectiveness of the one or more chemotherapeutic agents by potentiating the anti-tumor activity of the one or more chemotherapeutic agents without increasing toxicity or other unwanted side effects.

In some embodiments, the compositions and methods for use with such compositions comprise administering to a subject a regimen of one or more chemotherapeutic agents with an inhibitor of soluble epoxide hydrolase (sEHi) and a non-steroidal anti-inflammatory drug (NSAID) that inhibits one or more enzymes selected from the group consisting of cyclo-oxygenase ("COX")-1, COX-2, and 5-lipoxygenase ("5-LOX"). In some embodiments, the regimen administered employs one or more chemotherapeutic agents and a dual inhibitor of sEH and COX2. In some embodiments, the regimen does not increase toxicity or adverse side effects as compared to administering the one or more chemotherapeutic agents alone. In some embodiments, the regimen decreases toxicity and/or adverse side effects as compared to administering the one or more chemotherapeutic agents alone.

In some embodiments, the NSAID is selected from the group consisting of aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, sodium salicylate, alkyl salicylate and disalicylate. In some embodiments, the inhibitor of a cyclo-oxygenase is a preferential or selective inhibitor of COX-2. In some embodiments, the preferential or selective inhibitor of COX-2 is selected from the group consisting of celecoxib, valdecoxib, lumiracoxib, etoricoxib, parecoxib, rofecoxib, nabumetone, meloxicam, and mixtures thereof.

In some embodiments, the regimen comprises administering the chemotherapeutic agent(s) together with the sEHi and the NSAID. In some embodiments, the regimen comprises administering the chemotherapeutic agent(s) separately from the sEHi and the NSAID. In some embodiments, the chemotherapeutic agent(s) and the sEHi and the NSAID are delivered by the same route of administration (e.g., oral, injectable, I.V., parenteral, infusion). In some embodiments, the chemotherapeutic agent(s) and the sEHi and the NSAID are delivered by different routes of administration. In some embodiments, co-administering to the subject the sEHi and the NSAID does not increase toxicity or adverse side effects of the one or more chemotherapeutic agents. In some embodiments, co-administering to the subject the sEHi and the NSAID decreases toxicity and/or adverse side effects of the one or more chemotherapeutic agents.

In some embodiments, the methods comprise administering to the subject a dual inhibitor of sEH and COX-2. In some embodiments, the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB).

Also provided herein are pharmaceutical compositions and treatment systems. In some embodiments the pharmaceutical compositions and treatment systems comprise one or more chemotherapeutic agents, an sEHi, an NSAID and optionally, a pharmaceutically acceptable excipient. In some embodiments the pharmaceutical compositions and treatment systems comprise one or more chemotherapeutic agents, a dual sEHi dual inhibitor of sEH and COX-2 and optionally, a pharmaceutically acceptable excipient.

In some embodiments of the methods, compositions and treatment systems with the combinations of single inhibitors or the dual inhibitors, the one or more chemotherapeutic agents are selected from the group consisting of alkylating agent(s), platinum-coordination complexe(s), nucleoside analog(s), anti-metabolite(s), plant alkaloid(s) and/or terpenoid(s), vinca alkaloid(s), podophyllotoxin(s), camptothecin(s), anthracycline(s), aromatase inhibitor(s), taxane(s), topoisomerase inhibitor(s), antibiotic(s), hormone(s), differentiating agent(s), kinase inhibitor(s) and antineoplastic agent(s). In some embodiments, the chemotherapeutic agent is a platinum coordination complex. In some embodiments, the platinum coordination complex is selected from the group consisting of cisplatin, carboplatin, oxaliplatin, nedaplatin, saraplatin, lobaplatin, heptaplatin, and mixtures thereof. In some embodiments, the chemotherapeutic agent is a nucleoside analog. In some embodiments, the nucleoside analog is a pyrimidine analog, e.g., a deoxycytidine analog. In some embodiments, the pyrimidine analog is selected from the group consisting of gemcitabine, cytarabine (a.k.a., cytosine arabinoside), capecitabine, 5-fluorouracil, 5 fluorodeoxyuridine, 5-fluorodeoxyuridine monophosphate, 5 azacytidine, and mixtures thereof. In some embodiments, the methods include a regimen of chemotherapeutic agents selected from cisplatin, carboplatin, gemcitabine and combinations thereof.

In some embodiments, the subject has a cancer selected from the group consisting of: bladder, ovarian, cervical, breast, testicular, prostate, head and neck, oral, esophageal, gastric, lung, pancreatic, skin, leukemia, colon and colorectal. In some embodiments, the subject is a mammal, e.g., a human, a canine or a feline.

DEFINITIONS

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 oxidase. As discussed further in a separate section below, while the use of unmodified EETs is the most preferred, derivatives of EETs, such as amides and esters (both natural and synthetic), EETs analogs, and EETs optical isomers and corresponding EPA and DHA derivatives, including omega-3-derived epoxides epoxyeicosatetraenoic acids (EEQs) and epoxydocosapentaenoic acids (EDPs), and their mimics, can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

"COX" is an abbreviation for "cyclo-oxygenase." Several COX enzymes have been identified. Two isozymes, COX-1 and COX-2, are recognized as of clinical significance, with COX-1 considered to be constitutively expressed and COX-2 considered to be inducible and more prevalent at sites of inflammation. See, e.g., Hawkey, Best Pract Res Clin Gastroenterol. 15(5):801-20 (2001).

As used herein, a "COX-1 inhibitor" denotes an agent that inhibits COX-1 more than it inhibits COX-2, while a "COX-2 inhibitor" denotes an agent that inhibits COX-2 more than it inhibits COX-1. All current non-steroidal anti-inflammatory drugs (NSAIDs) inhibit both COX-1 and COX-2, but most tend to inhibit the two isoforms to different degrees. Since both enzymes tend to be inhibited together to some degree, one can consider an inhibitor of either enzyme to be "COX inhibitor".

"LOX" is an abbreviation for "lipoxygenase." Several LOX enzymes have been identified. Arachidonate 5-lipoxygenase ("5-LOX", EC 1.13.11.34) is involved in the production of pro-inflammatory mediators. Arachidonate 12-lipoxygenase ("12-LOX", EC 1.13.11.31) and arachidonate 15-lipoxygenase ("15-LOX", EC 1.13.11.33) form trihydroxytetraenes known as "lipoxins" ("lipoxygenase interaction products") from arachidonic acid. Lipoxins act as local anti-inflammatory agents.

"5-lipoxygenase activating protein," or "FLAP," is a protein required before 5-LOX can become catalytically active. Inhibiting FLAP activity reduces or prevents 5-LOX activation, decreasing the biosynthesis of leukotrienes.

"$IC_{50}$" refers to the concentration of an agent required to inhibit enzyme activity by 50%.

The term "therapeutically effective amount" refers to that amount of the compound being administered sufficient to prevent or decrease the development of one or more of the symptoms of the disease, condition or disorder being treated (e.g., cancer, tumor burden, metastasis).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 71st Ed., 2017 (PDR Network), PDR Network, or Brunton and Knollmann, Goodman & Gilman's The Pharmacological Basis of Therapeutics, 13th edition, 2017, McGraw-Hill Education/ Medical). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., $21^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., a chemotherapeutic agent, including a platinum coordination complexing agent, a pyrimidine analog, an inhibitor of sEH, an inhibitor of COX-2, and mixtures thereof), optionally with an anti-inflammatory agent and/or an analgesic agent) to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (e.g., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "subject" or "individual" interchangeably refers to a mammal, e.g., a human, a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the cancer in a non-human mammalian subject by a measurable amount (e.g., tumor burden or metastasis) using any method known in the art. For example, cancer is inhibited, reduced or decreased if an indicator of cancer, e.g., tumor burden, metastasis, is at least about 10%, 20%, 30%, 50%, 80%, or 100% reduced, e.g., in comparison to the same inflammatory indicator prior to co-inhibition of sEH and COX-2 (e.g., via one or multiple agents). In some embodiments, the cancer is inhibited, reduced or decreased by at least about 1-fold, 2-fold, 3-fold, 4-fold, or more in comparison to the cancer prior to co-inhibition of sEH and COX-2. Indicators of cancer can also be qualitative.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxy fatty acids (EpFA) (e.g., an inhibitor of sEH, an EET, an epoxy fatty acid, and mixtures thereof) and/or an anti-inflammatory agent.

BRIEF DESCRIPTION OF THE DRAWINGS

FIGS. 2A-D illustrate that PTUPB potentiates cisplatin anti-tumor activity. A, Tumor growth in NSG-PDX bladder cancer mouse model BL0293. When tumor volume of the tumor reached ~100-200 cm3, mice were administered by i.v. with PEG 300 control, single agent cisplatin (2 mg/kg, i.v., Day 1, 2, 3, 15, 16, and 17, black arrows), single agent PTUPB (30 mg/kg, orally, once daily for up to 30 days), or cisplatin (2 mg/kg) plus PTUPB (30 mg/kg) in combination. The tumor dimensions were measured every 3 to 4 days. The tumor volume was calculated using the formula: 0.5×length×width$^2$ (mm$^3$). Mice were euthanized when the tumor length reached 20 mm in any direction. The median time of the tumor growth to 7.5×BL (blacked dotted line) was 20 days for the control and 24.4 days in the PTUPB group (p=0.085) and 35.8 days in the cisplatin group (p=0.0003). The median time of the cisplatin and PTUPB combination group was significantly increased to 47.8 days compared to PTUPB (p<0.0001) or cisplatin (p=0.002) monotherapy groups. B, Overall survival with statistical analysis. Overall survival of the combination treatment group was 60.9 days, significantly longer than that of either PTUPB (39.4 days, p=0.007) or cisplatin (47 days, p=0.02) monotherapy groups. C, Tumor growth in the NSG-PDX bladder cancer mouse model BL0269. Mice were euthanized on day 29 and the tumors were collected. The representative images of the excised tumors are shown. D, Tumor growth in the NSG-PDX bladder cancer mouse model BL0269. When the size of the tumor xenografts reached around 0.1~0.2 cm3, the NSG mice were treated with PEG 300 control, PTUPB (30 mg/kg, orally, once daily for up to 30 days), cisplatin (2 mg/kg, i.v., Day 1, 2, 3, 15, 16, and 17, black arrows), gemcitabine (150 mg/kg, i.p. weekly for 4 weeks), and cisplatin (2 mg/kg) plus gemcitabine (150 mg/kg) plus PTUPB (30 mg/kg) combination. The tumor sizes were measured every 3 to 4 days. The tumor volume was calculated using the formula: 0.5×length×width$^2$ (mm$^3$).

FIGS. 3A-B illustrate tumor growth in the NSG-PDX bladder cancer mouse model BL0269. A, Celecoxib does not potentiate cisplatin effect in BL0269. When the volume of the tumor xenografts reached approximately 100~200 cm$^3$, mice were treated with PEG 300 control, single agent cisplatin (2 mg/kg, i.v., Day 1, 2, 3, 15, 16, and 17, red arrows), single agent celecoxib (30 mg/kg, orally, once daily), and cisplatin (2 mg/kg) plus celecoxib (30 mg/kg) combination. The tumor dimensions were measured every 3~4 days. The tumor volume was calculated using the formula: 0.5×length×width$^2$ (mm$^3$). B, t-AUCB moderately potentiate cisplatin effect in PDX BL0269. When the volume of the tumor xenografts reached approximately 100~200 cm$^3$, mice were treated with PEG 300 control, single agent cisplatin (2 mg/kg, i.v., Day 1, 2, 3, 15, 16, and 17, red arrows), single agent PTUPB (30 mg/kg, orally, once daily), single agent t-AUCB (3 mg/kg, orally, once daily), and cisplatin (2 mg/kg) plus PTUPB (30 mg/kg) or t-AUCB (3 mg/kg) combination. The tumor dimensions were measured every 3 to 4 days. The tumor volume was calculated using the formula: 0.5×length×width$^2$ (mm$^3$).

FIGS. 4A-C illustrate body weight change during PDX bladder cancer mice experiment. A, BL0293 mice treated with cisplatin (2 mg/kg), PTUPB (30 mg/kg) and cisplatin (2 mg/kg)+PTUPB (30 mg/kg). Compared to the control group, PTUPB slightly decreased body weight while cisplatin treatment led to more weight loss. Addition of PTUPB did not further increase the weight loss. B, BL0269 mice treated with cisplatin (2 mg/kg), PTUPB (30 mg/kg) and cisplatin (2 mg/kg)+PTUPB (30 mg/kg). C, BL0269 mice treated with PTUPB (30 mg/kg), gemcitabin (150 mg/kg)+cisplatin (2 mg/kg) and PTUPB+GC. No significant behavioral abnormality was observed among any of these groups. N=6-8 mice per group.

FIGS. 5A-D illustrate blood counts, Hemoglobin and Platelets determination and biochemistry panel. A and B, blood specimens were collected 6 d and 20 d after the first dose of treatment. No significant changes in the blood counts were observed between treatment groups. At Day 6, compared to the control group of white blood cell (WBC) count of 7.19 k/ul, the WBC count of PTUPB, cisplatin and the combination treatment were 7.94 k/µl (p=0.889), 3.69 k/µl (p=0.426) and 3.23 k/µl (p=0.376), respectively. At day 20, compared to the control group of white blood cell (WBC) count of 28.57 k/µl, the WBC count of PTUPB, cisplatin and the combination treatment were 12.96 k/µl (p=0.337), 3.25 k/µl (p=0.394) and 2.63 k/µl (p=0.387). Because of large individual variations, we did not see any statistical significance. As an alkylating agent, cisplatin seemed to decrease WBC count, but addition of PTUPB to cisplatin did not further decrease WBC count. We did not observe any statistically significant difference of hemoglobin and platelet count among these four groups. C and D, blood specimens were collected 6 d and 20 d after the first dose of treatment. No significant damage to liver and kidney in any of these groups as demonstrated in the liver function of aspartate transaminase (AST) and total bilirubin, and in the kidney function of blood urea nitrogen (BUN) and creatinine. AST: aspartate transaminase; BUN: alanine transaminase.

FIGS. 9A-B illustrate that PTUPB combined with cisplatin modulates p-ERK and p-AKT in tumor tissue. A, Western blot analysis of protein expression of indicated phosphoproteins, total proteins and loading control GAPDH. Protein was extracted at indicated times from PDX BL0293 tumors treated with cisplatin, PTUPB or cisplatin plus PTUPB combination therapy. B, Illustration of relevant signaling pathways indicating possible roles for sEH and COX-2.

FIGS. 10A-C illustrate that PTUPB does not alter carboplatin-DNA adduct levels. A, Cultures of the ATCC bladder cancer cell line 5637 were incubated with 100 μM [14C] carboplatin in the presence (gray bar) or absence (white bar) of 10 μM PTUPB for 4 h or 4 h then washed and further incubated 20 hr with fresh drug-free culture medium. B, 5637 cells were pretreated (grey bar) with 10 μM PTUPB for 5 h before cells were exposed to 100 μM [$^{14}$C]carboplatin for indicated amount of time. C, NSG mice carrying BL0293 tumors were treated with 37.5 mg/kg (therapeutic dose) carboplatin (50,000 dpm/g) via IV bolus and tissue was harvested after 24 hr. PTUPB (30 mg/kg in PEG400) was administered via oral gavage 16 hr (grey bar) or 1 hr (black bar) before carboplatin dosing. Sample size for the cell line experiments was N=3, sample size for PDX in experiments was N=6 (carbo alone) or 3 (in both PTUPB groups).

FIGS. 11A-B PTUPB illustrate that increases cisplatin cytotoxicity in the 5637 bladder cancer cell line. Dose-response curves of 5637 cells treated with cisplatin and PTUPB at different concentrations as determined in a 72 hr cell viability assay. A, Single drug treatment. Cultures of 5637 cells were treated with different concentrations of PTUPB or cisplatin (0, 0.01, 0.1, 1, 2, 5, 10, 20, 50, and 100 μM). B, Combination drugs treatment. 5637 cells were treated with different concentrations of cisplatin (0, 0.01 0.1, 0.5, 1, 2, 5, 10, and 100 μM) in combination with different concentrations of PTUPB (1, 2, 5, and 10 μM). Sample size for the cell line experiments was N=3. *CI: Combination Index.

FIGS. 12A-C illustrate that PTUPB did not increase cisplatin cytotoxicity in the J82 (A), TCCSUP (B) and T24 (C) and bladder cancer cell lines. Dose-response curves of bladder cancer cells treated with cisplatin and PTUPB at different concentrations as determined in a 72 hr cell viability assay. Cells were treated with different concentrations of cisplatin (0, 0.01 0.1, 0.5, 1, 2, 5, 10, 100 μM) in combination with different concentrations of PTUPB (1, 2, 5, 10 μM).

FIGS. 14A-C illustrate that PTUPB extends gemcitabine chemotherapy efficacy (A), increases tumor specific survival (B) and does not increase gemcitabine toxicity (C) in bladder cancer PDX. PDX BL0808 was implanted into immunodeficient nod scid gamma (NSG) mice and treatment was started once tumor volume reached approximately 250 mm³. Treatment consisted of either vehicle (5 μL/g PEG300, p.o., once daily until end of study), PTUPB (30 mg/kg in PEG300, p.o., once daily until end of study), gemcitabine (150 mg/kg in WFI, IP, once weekly, 4 times) or a combination of PTUPB with gemcitabine. Tumor volume and animal weight was monitored every other day and mice were sacrificed once tumor size reached 2 cm and tumor specific survival was recorded.

DETAILED DESCRIPTION

1. Introduction

Cisplatin therapy involves modulation of the arachidonic acid (ARA) pathway, which plays numerous roles in inflammation and tumorigenesis. Eicosanoids are lipid mediators derived from ARA by cyclooxygenases (COXs), lipoxygenases (LOXs) and cytochrome P450s (CYPs). Among them, a COX-2 mediated metabolite, prostaglandin E2 (PGE2), is pro-inflammatory and pro-angiogenic (4). COX inhibitors, both nonsteroidal anti-inflammatory drugs (NSAIDs) and COX-2 selective inhibitors (coxibs), have been widely used to treat inflammation and pain. Separately, epoxyeicosatrienoic acids (EETs), derived from the metabolism of ARA by CYP epoxygenases, have potent anti-inflammatory, analgesic, antihypertensive, cardio-protective, and organ-protective properties. However, EETs are rapidly metabolized to inactive diols by soluble epoxide hydrolase (sEH). sEH inhibitors (sEHIs) maintain the level of EETs in vivo, and are now in development for treatment of various diseases. In preclinical studies as well as in clinical trials, sEHIs have displayed excellent safety profiles.

EETs transcriptionally inhibit the expression of COX-2 and thus decrease the production of PGE2. Interestingly, COX-2 overexpression in tumor or stromal cells leads to tumor angiogenesis and coxibs block the production of angiogenic factors, leading to inhibition of proliferation, migration, and vascular tube formation. However, targeting this single component of the ARA pathway with coxibs has failed in human clinical trials for several cancers. Furthermore, sEHIs synergize the analgesic and anti-inflammatory effects of coxibs, prevent gastrointestinal erosion, and alter prostacyclin (PGI2) and thromboxane A2 (TBX2) ratios associated with blood clotting. It is desirable to inhibit both COX-2 and sEH in order to maximize antitumor activity and reduce toxic effects of selective COX-2 inhibition. This dual COX-2/sEH inhibition strategy also may have the potential to protect normal tissues from cisplatin and other chemtotherapeutic agent toxicity.

Figure 1:
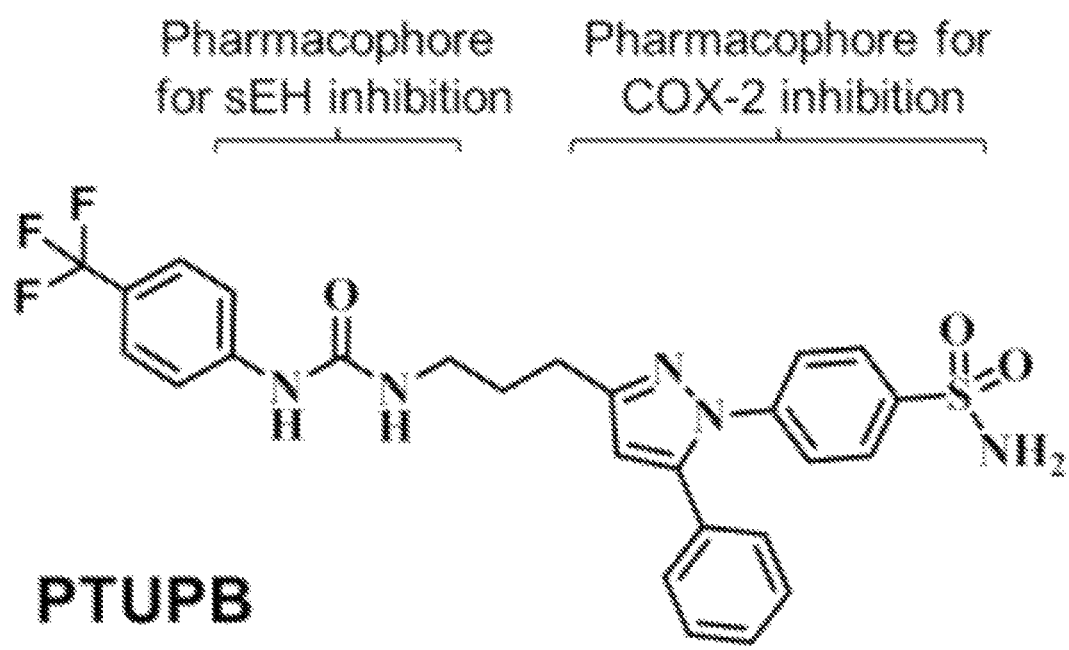
FIG. 1 illustrates the chemical structure of a COX-2/sEH dual inhibitor, 4-(5-phenyl-3-{3-[3-(4-trifluoromethyl-phenyl)-ureido]-propyl}-pyrazol-1-yl)-benzenesulfonamide (PTUPB).

We recently demonstrated that a combination treatment of celecoxib and the sEHI inhibitor t-AUCB has synergistic effects for blocking angiogenesis and tumorigenesis in two mouse models of cancer (20). A compound that concurrently inhibits both COX-2 and sEH called (4-(5-phenyl-3-{3-[3-(4-trifluoromethyl-phenyl)-ureido]-propyl}-pyrazol-1-yl)-benzenesulfonamide; PTUPB) (FIG. 1) (21) is more effective at inhibiting primary tumor growth and metastasis compared to inhibitors selective to either pathway, either as single agents or in combination. PTUPB acts, in part, by suppressing tumor angiogenesis via selective inhibition of endothelial cell proliferation, without any obvious cytotoxic effects in mice (20).

Cisplatin-based therapy is highly toxic, but moderately effective in most cancers. Concurrent inhibition of cyclooxygenase-2 (COX-2) and soluble epoxide hydrolase (sEH) results in anti-tumor activity, and has organ protective effects. We determined the anti-tumor activity of PTUPB, an orally bioavailable COX-2/sEH dual inhibitor, in combination with cisplatin and gemcitabine (GC) therapy. NSG mice bearing bladder cancer subject-derived xenografts were treated with vehicle, PTUPB, cisplatin, GC or combinations thereof. Mouse experiments were performed with two different PDX models. PTUPB potentiated cisplatin and GC therapy, resulting in significantly reduced tumor growth and prolonged survival. PTUPB plus cisplatin was no more toxic than cisplatin single agent treatment as assessed by body weight, histochemical staining of major organs, blood counts and chemistry.

We demonstrate that the combination of PTUPB and cisplatin-based therapy potentiates anti-tumor activity without increasing cisplatin toxicity. We extended our work to include recently developed immunodeficient nod scid gamma (NSG) mice bearing subject-derived xenografts (PDX) of bladder cancer (22), and conducted additional mechanistic studies. We observed that in vivo PTUPB potentiated cisplatin efficacy without increasing toxicity. PTUPB also improved in vivo response to GC therapy. Platinum-DNA adducts were not modulated by PTUPB exposure, indicating an orthogonal mechanism of action compared to DNA alkylation.

PTUPB enhances apoptosis and downregulates proliferation signaling, especially when combined with cisplatin. The combination of PTUPB and cisplatin increased apoptosis and decreased phosphorylation in the MAPK/ERK and PI3K/AKT/mTOR pathways compared to controls. PTUPB treatment did not alter platinum-DNA adduct levels, which is the most critical step in platinum-induced cell death. The combination index method showed modest synergy between PTUPB and platinum agents in the 5637 cell line, but not in other cell lines. In conclusion, PTUPB potentiated the anti-tumor activity of cisplatin-based treatment without increasing toxicity in vivo, and provides a combination chemotherapy partner.

2. COX, LOX and sEH

Inhibition of the enzyme known as "soluble epoxide hydrolase" ("sEH") reduces inflammation. See, U.S. Pat. No. 6,150,415. Cis-Epoxyeicosatrienoic acids ("EETs") are substrates sEH hydrolyzes; it is in part the increase in the levels of EETs by inhibiting sEH that results in the anti-inflammatory effect seen when sEH inhibitors ("sEHIs") are administered.

It has been demonstrated that inhibition of COX-1 and/or COX-2 results in a rise in EET levels. This effect is consistent with the conclusion that some or all of the anti-inflammatory effect and analgesic effects seen from the use of COX-1 and COX-2 inhibitors result only not only from blocking the formation of prostaglandins and other downstream, pro-inflammatory metabolites, as has been believed in the art, but also from the rise in EET levels. Further, the studies underlying the present invention reveal that the rise in levels of EETs from the action of inhibitors of COX-1 or COX-2 further increases dramatically in the presence of sEHIs. See, U.S. Pat. No. 7,951,831.

The observation that inhibition of COX-1 and/or COX-2 results in a rise in EET levels several related implications. First, to the extent that the analgesic effects of COX-1 and -2 inhibitors are due to their effect on increasing the levels of EETs, sEHI's, which also increase the levels of EETs in the body, are also analgesics. Compounds which stabilize EETs or which mimic them likewise have analgesic properties, either by acting as EETs or by acting as a decoy for sEH, thereby reducing the rate at which endogenous EETs are hydrolyzed and maintaining their levels in the body for a longer period.

The analgesic effect of EETs and their mimics is augmented by the fact that EETs are believed to inhibit activation of nuclear factor κ-KB (NF-κB) and to inhibit the nuclear translocation of NF-κB. This in turn reduces activation of a variety of proinflammatory peptides and proteins, such as COX-2. Our studies indicate that COX-2 levels are reduced at 6, 12, and 24 hours after exposure to inflammation mediators when sEHIs are administered. Thus, in addition to the direct effect on reducing pain and inflammation due to increasing the level of EETs, sEHIs also reduce pain and inflammation indirectly at the level of transcription and protein induction. Because the rate at which EETs are degraded is reduced by the presence of the sEHIs, the analgesic effect can be increased by administering EETs with or in conjunction with the sEHI.

Second, the dramatic increases in EET levels seen when both a COX inhibitor and a sEHI are co-administered indicate that sEHI's act synergistically with inhibitors of COX-1 and of COX-2 in increasing EET levels. As noted, we have discovered that COX-1 and COX-2 inhibitors increase the levels of EETs present in the body. The presence of sEHIs slows the hydrolysis of the EETs to their corresponding diols, thereby increasing the effect of the COX inhibitors. Any given dosage of the COX-1 or COX-2 inhibitor will therefore have a stronger effect, and a lower dosage will be needed to achieve a given reduction in pain or inflammation. Since the side effects of COX-2 inhibitors are considered to be dose related, the ability to be able to reduce the dosage of COX-2 inhibitor necessary to achieve any given amount of pain relief also reduces the side effects related to use of the COX-2 inhibitor. As reported in the U.S. Pat. No. 7,951,831, studies of the effects of co-administering COX-2 inhibitors and sEHI resulted in lowering the levels of metabolites considered to be indicators of increased risk of heart attack or stroke.

The joint effect of both a COX inhibitor and an sEHI should be generally applicable to downstream metabolites of epoxylipins not involving diol formation. As will be explained in more detail below, and without wishing to be bound by theory, it is believed that the sEHI and the COX inhibitors act by two separate mechanisms. Again without wishing to be bound by theory, it is believed that the combination of the two mechanisms is responsible at least in part for the synergistic effects on pain and inflammation seen in combining the two different types of inhibitors.

As noted, EETs inhibit the activation and nuclear translocation of NF-κB. This in turn reduces activation of a variety of proinflammatory peptides and proteins, such as COX-2. Thus, the sEHIs reduce the amount of COX-2 present and this, in turn, reduces the amount of inhibitor of COX-2 needed to block the formation of pro-inflammatory metabolites. The use of sEHIs in conjunction with a COX-1 or COX-2 inhibitor, or both, therefore improves the anti-inflammatory effects of the COX-1 or COX-2 inhibitor, while simultaneously reducing the side effects associated with the COX-1 or COX-2 inhibitor.

Third, another group of enzymes involved in arachidonic acid metabolism are the lipoxygenases ("LOX"). The LOX enzymes, and especially the enzyme known as "5-LOX", are implicated in inflammation through their activation of pro-inflammatory substances called leukotrienes. In the absence of sEHIs, the inhibition of COX enzymes results in increasing the flow of arachidonic acid metabolites through the LOX pathway, and increases the production of the pro-inflammatory leukotrienes. Similarly, it is believed that inhibition of the LOX pathway shuttles more arachidonate into other pathways in the arachidonate cascade, including the COX pathways, leading to increased amounts of inflammatory mediators. Thus, the use of sEHIs in conjunction with an inhibitor of 5-LOX can potentiate the anti-inflammatory effects of the LOX inhibitor, while simultaneously reducing its side effects. One of the factors in the activation of 5-LOX is 5-lipoxygenase activating protein, usually abbreviated as "FLAP." Inhibitors of FLAP, such as MK886 (Merck Co., Darm-stadt, Germany), DG-031 (Decode Genetics Inc., Reykjavik, Iceland), and BAY X 1005 ((R)-2[4-(quinolin-2-yl-methoxy)phenyl]-2-cyclopentyl acetic acid, Bayer A G, Leverkusen, Germany). See, e.g., Harkonarson et al., JAMA, 293(18):2277-9 (2005), Mancini et al., J Biol Chem, 273(49):32842-32847 (1998); Burchhardt and Muller-Peddinghaus, Prostaglandins Leukot Essent Fatty Acids. 60(1):5-11 (1999); Hatzelmann et al., Biochem Pharmacol. 45(1):101-11 (1993); Titos et al., FASEB J. 17:1745-1747 (2003). Thus, 5-LOX can be inhibited directly by a 5-LOX inhibitor, or indirectly, by inhibiting FLAP, which would otherwise activate 5-LOX.

The compositions and methods of the invention have a number of benefits. First, the methods and compositions elevate mediators with favorable effects and, to the extent that they reduce the formation of COX, reduce the production of pro-inflammatory metabolites. Second, the metabolites of sEH are not known to have significant roles in controlling homeostasis. Thus, the adverse side effects and adverse drug interactions seen in directly inhibiting COX-2 is not a factor with the use of sEHI. Third, whereas it has recently been noted that COX-2 inhibitors delay the resolution of inflammation, sEHI are believed to induce the formation of the pro-resolution lipid mediator Lipoxin A4. Therefore, use of sEHI in combination with COX-1, COX-2, or 5-LOX inhibitors are expected to reduce pro-inflammatory gene and protein expression, while promoting healing. Further, recent reports have indicated that high levels of COX inhibitors are linked to increased risk of heart attack or stroke, and have led to a reduced use of COX inhibitors. The discoveries of the invention indicate that COX inhibitors can be effective at lower levels, diminishing the risk to the subject.

sEHI can be administered without the side effects that COX-2 inhibitors have shown. And, as noted above, since the combination of an sEHI and a COX-2 inhibitor permits achieving a given amount of effect (such as a given amount of pain relief) with a lower level of COX-2 inhibitor than would be necessary in the absence of the sEHI, the use of the combination reduces the side effects that would otherwise be due to the amount of COX-2 inhibitor that would otherwise be necessary to achieve the same result.

COX-2 inhibitors and sEHI reduce inflammation by different means. COX-2 inhibitors are known to inhibit COX-2 activity, while sEHI do not directly inhibit the activity of COX-2, but reduce the amount of COX-2 that would otherwise be inducted by inflammatory agents. As noted above, without wishing to be bound by theory, these different mechanisms of action, previously unknown, may be responsible in part for the synergistic effects seen in combining the use of the two types of agents.

3. Subjects Amenable to Treatment

Co-inhibition of soluble epoxide hydrolase (sEH) and a COX and/or LOX inhibitor potentiates that antitumor effects of and prolongs survival in subjects receiving a regime of one or more chemotherapeutic agents, e.g., a platinum coordination complex chemotherapy agent, a pyrimidine analog, alone or in combination. The co-inhibition of sEH and COX and/or LOX can be effected with a single dual-inhibiting agent or multiple agents. Co-inhibition of sEH and COX and/or LOX potentiates the inhibition, reduction, retraction or prevention of proliferation or growth of a tumor or a cancer cell effected by therapy with one or more chemotherapeutic agents, e.g., a platinum coordination complex chemotherapy agent (e.g., cisplatin, carboplatin, oxaliplatin, nedaplatin, saraplatin, lobaplatin, heptaplatin, an mixtures thereof), a pyrimidine analog (e.g., gemcitabine, cytarabine (a.k.a., cytosine arabinoside), capecitabine, 5-fluorouracil, 5 fluorodeoxyuridine, 5-fluorodeoxyuridine monophosphate, 5 azacytidine), alone or in combination. In the context of effecting treatment, the subject has a cancer or a tumor burden, and administration of one or multiple agents that inhibit sEH and inhibit COX and/or LOX can reverse, delay or inhibit progression of a cancer being treated by a regime of one or more chemotherapeutic agents, e.g., a platinum coordination complex chemotherapy agent, alone a pyrimidine analog, alone or in combination. In the context of effecting prevention, the subject may be in remission, or may have undergone the removal of a primary tumor, and further co-inhibition of sEH and COX-1 in combination with administration of one or more chemotherapeutic agents, e.g., platinum coordination complex and/or pyrimidine analog chemotherapy, can reduce, inhibit or eliminate growth of metastasis. The subject may or may not already be undergoing a regime of one or more chemotherapeutic agents, e.g., a regime of a platinum coordination complex chemotherapeutic agent and/or a pyrimidine analog.

Exemplary cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation lymphoma, lung cancer, breast cancer, ovarian cancer, cervical cancer, prostate cancer, testicular cancer, gastric and intestinal cancers (including colon cancer and rectal cancer), hepatic cancer, oral cancer, esophageal cancer, bladder cancer, renal cancer, bladder cancer, head and neck cancers. In some embodiments, the cancer produces solid tumors. In some embodiments, the cancer is an epithelial cancer or a carcinoma, a sarcoma, or a hematological cancer.

Exemplary hematologic malignancies that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation lymphomas (such as but not limited to, non-Hodgkin's lymphoma, including Burkitt's lymphoma, and Hodgkin's lymphoma, as well as all subtypes associated with each), acute lymphocytic leukemia (ALL), chronic lymphocytic leukemia (CLL), acute myeloid leukemia (AML), chronic myeloid leukemia (CML), and adult T-cell leukemia lymphoma.

Exemplary lung cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation adenocarcinoma, squamous carcinoma, bronchial carcinoma, broncoalveloar carcinoma, large cell carcinoma, small-cell carcinoma, non-small cell lung carcinoma and metastatic lung cancer refractory to conventional chemotherapy.

Exemplary hematological cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation leukemia, multiple myeloma and plasmocytoma.

Exemplary sarcomas that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation rhabdomyosarcoma, osteosarcoma, chondrosarcoma, myosarcoma, liposarcoma, fibrosarcoma and Ewing's sarcoma.

Exemplary gastric, digestive and intestinal cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation intestinal carcinoma, rectal carcinoma, colon carcinoma, familial adenomatous polyposis carcinoma, hereditary non-polyposis colorectal cancer, gastric carcinoma, craniopharyngioma, gall bladder carcinoma, esophageal carcinoma, pancreatic carcinoma and adenocarcinoma (including adenocarcinomas of the esophagus and stomach).

Exemplary cancers of the head and neck that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation larynx carcinoma, hypopharynx carcinoma, tongue carcinoma and salivary gland carcinoma.

Exemplary urogenital cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation labial carcinoma, ovarian carcinoma, cervix carcinoma, uterine corpus carcinoma, endometrium carcinoma, chorion carcinoma, prostate carcinoma, testis carcinoma, seminoma, urinary carcinoma, kidney carcinoma, renal carcinoma, and adenocarcinoma (including adenocarcinomas of the vagina, cervix, prostate, and urachus).

Exemplary nervous and sensory system cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation neuroblastoma, brain tumors, meningioma, ependymoma, medulloblastoma, peripheral neuroectodermal tumors, glioblastoma, astrocytoma, oligodendroglioma and retinoblastoma.

Exemplary endocrine and glandular tissue cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation pancreatic carcinoma, medullary thyroid carcinoma, follicular thyroid carcinoma, anaplastic thyroid carcinoma, papillary thyroid carcinoma, pheochromocytoma, adrenal tumors and adenocarcinoma.

Exemplary hepatic cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation hepatocellular carcinoma.

Exemplary skin cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation melanoma, basal cell carcinoma, squamous cell carcinoma and choroids melanoma.

Additional cancers that can be treated or prevented by co-inhibition of sEH and COX and/or LOX in combination with an anti-inflammatory agent in combination with one or more chemotherapeutic agents, e.g., a regime of a platinum coordination complex chemotherapeutic agent and/or a pyrimidine analog, include without limitation teratomas.

4. Chemotherapeutic Agents

In the present methods, a subject in need of treatment for cancer is undergoing or about to begin a regime of one or more chemotherapeutic agents, e.g., a regime of a platinum coordination complex chemotherapeutic agent and/or a pyrimidine analog. The anticancer effects of the one or more chemotherapeutic agents are potentiated or enhanced by concurrent co-inhibition of sEH and COX and/or LOX, thereby increasing tumor reduction, promoting tumor retraction, inhibiting or delaying metastasis and prolonging survival of the subject, e.g. in comparison to administration of the chemotherapy regime without co-inhibition of sEH and COX and/or LOX.

Examples of chemotherapeutic agents that can be co-administered with the agent that inhibit sEH and COX and/or LOX are known in the art and include without limitation alkylating agent(s) (e.g., nitrogen mustards, nitrogen ureas, ethylenimines, methylmelamines, alkyl sulfonates, carmustine, triazenes), platinum-coordination complexes (e.g., cisplatin, carboplatin, oxaliplatin, nedaplatin, saraplatin, lobaplatin, heptaplatin, and mixtures thereof), anti-metabolite(s) (e.g., folic acid analogs (e.g., methotrexate), pyrimidine analogs (e.g., capecitabine, 5-fluorouracil, 5-fluorodeoxyuridine, 5-fluorodeoxyuridine monophosphate, cytosine arabinoside, 5-azacytidine, gemcitabine), purine analogs (e.g., mercaptopurine, thioguanine, azathioprine, pentostatin, erythrohydroxynonyladenine, fludarabine, cladribine)), plant alkaloid(s) and/or terpenoid(s), vinca alkaloid(s) (e.g., vincristine, vinblastine, vinorelbine, and vindesine), podophyllotoxin(s) (e.g., etoposide and teniposide), camptothecin(s) (e.g., irinotecan and topotecan), anthracycline(s), aromatase inhibitor(s), taxane(s) (e.g., paclitaxel, taxol and docetaxel), topoisomerase inhibitor(s) (e.g., (Type I inhibitors: camptothecins, including irinotecan and topotecan; Type II Inhibitors: amsacrine, etoposide, etoposide phosphate, and teniposide), antibiotic(s) (e.g., dactinomycin, daunorubicin, doxorubincin, idarubicin, epirubicin, bleomycins, mitomycin), hormone(s), differentiating agent(s), kinase inhibitor(s) (e.g., Bevacizumab, BIBW 2992, Cetuximab, Imatinib, Trastuzumab, Gefitinib, Ranibizumab, Pegaptanib, Sorafenib, Dasatinib, Sunitinib, Erlotinib, Nilotinib, Lapatinib, Panitumumab, Vandetanib, E7080, Pazopanib, Mubritinib and Fostamatinib) and anti-neoplastic agent(s) (e.g., (dactinomycin, doxorubicin, epirubicin, fludarabine and bleomycin). Any chemotherapeutic agent being used to treat the cancer of interest can be co-administered in a combination therapy regime with the agent that increases EETs (e.g., an inhibitor of sEH, an EET, an EpDPE, an EpETE, and mixtures thereof). Chemotherapeutic agents of use are known in the art and described in reference texts, e.g., Physicians' Desk Reference, 71st Ed., 2017, PDR Network or Brunton and Knollmann, Goodman & Gilman's The Pharmacological Basis of Therapeutics, 13th edition, 2017, McGraw-Hill Education/Medical.

a. Platinum Coordination Complex Agents

In certain embodiments, the chemotherapy regime entails the co-administration of a platinum coordination complex. Platinum coordination complex chemotherapy agents for use in the chemotherapy regime can include cisplatin, carboplatin, oxaliplatin, nedaplatin, saraplatin, lobaplatin, heptaplatin, and mixtures thereof. In some embodiments, concurrent co-inhibition of sEH and COX and/or LOX allows for reduced or subtherapeutic dosing of the platinum coordination complex chemotherapeutic agent.

b. Pyrimidine Analogs

In certain embodiments, the chemotherapy regime entails the co-administration of a pyrimidine analog. Pyrimidine analog chemotherapy agents for use in the chemotherapy regime can include gemcitabine, cytarabine (a.k.a., cytosine arabinoside), capecitabine, 5-fluorouracil, 5 fluorodeoxyuridine, 5-fluorodeoxyuridine monophosphate, 5 azacytidine, and mixtures thereof. In some embodiments, concurrent co-inhibition of sEH and COX and/or LOX allows for reduced or subtherapeutic dosing of the pyrimidine chemotherapeutic agent.

5. Potentiating Agents

The anticancer effects of the one or more chemotherapeutic agents, e.g., a regime of a platinum coordination complex chemotherapeutic agent and/or a pyrimidine analog, are potentiated or enhanced by concurrent co-inhibition of sEH and COX and/or LOX, thereby increasing tumor reduction, promoting tumor retraction, inhibiting or delaying metastasis and prolonging survival of the subject, e.g. in comparison to administration of the chemotherapy regime without co-inhibition of sEH and COX and/or LOX.

a. Dual Inhibitors of sEH and COX-2

In some embodiments, the subject is administered a single compound for co-inhibition with two pharmacophores: one for inhibition of sEH and a second for inhibition of COX-2, e.g., a compound that is a dual inhibitor of sEH and COX-2. Illustrative sEH/COX-2 dual inhibitor agents are described, e.g., in WO 2012/082647 and in Hwang, et al., (2011) J Med Chem. 54(8):3037-50, can find use in the present methods. In some embodiments, the sEH/COX-2 dual inhibitor agent is 4-(5-phenyl-3-{3-[3-(4-trifluoromethyl-phenyl)-ureido]-propyl}-pyrazol-1-yl)-benzenesulfonamide (PTUPB).

b. Inhibitors of sEH

In some embodiments, the agent for inhibition of sEH is separate from the agent for inhibition of COX-2. Scores of sEH inhibitors are known, of a variety of chemical structures. Inhibitors of sEH are currently reviewed in Kodani, et al., *Drug Metabolism and Disposition* (2015) 43(5):788-802. Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12 carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. Derivatives that are metabolically stable are of use, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999).

Derivatives of urea are transition state mimetics that form a group of sEH inhibitors. Within this group, N,N'-dodecyl-cyclohexyl urea (DCU), is an inhibitor, while N-cyclohexyl-N'-dodecylurea (CDU) is a particular embodiment. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. Both the 1- and the 2-adamantyl ureas have been tested and have about the same high activity as an inhibitor of sEH. Adamantyl ureas of use include, e.g., 12-(3-Adamantan-1-yl-ureido)dodecanoic acid (AUDA), 12-(3-Adamantan-1-yl-ureido)dodecanoic acid butyl ester (AUDA-BE), and Adamantan-1-yl-3-{5-[2-(2-ethoxyethoxy)ethoxy]pentyl}urea (AEPU).

Another group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1
IC$_{50}$ values for selected alkylpiperidine-based sEH inhibitors against human sEH
| R: | | Compound (n = 0) | IC$_{50}$ (μM)$^a$ | Compound (n = 1) | IC$_{50}$ (μM)$^a$ |
|---|---|---|---|---|---|
| H | | I | 0.30 | II | 4.2 |
| 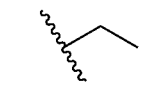 | | 3a | 3.8 | 4.a | 3.9 |
| | | 3b | 0.81 | 4b | 2.6 |
| | | 3c | 1.2 | 4c | 0.61 |
| 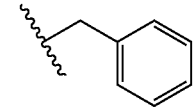 [SMILES: *Cc1ccccc1] | | 3d | 0.01 | 4d | 0.11 |
$^a$As determined via a kinetic fluorescent assay.

TABLE 2 sEH inhibitors

| Structure | Name | sEHi # |
|---|---|---|
| 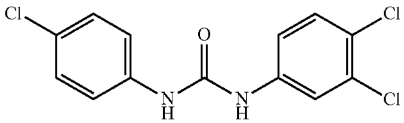 [SMILES: O=C(Nc1ccc(Cl)cc1)Nc1ccc(Cl)c(Cl)c1] | 3-(4-chlorophenyl)-1-(3,4-dichlorphenyl)urea or 3,4,4'-trichlorocarbanilide | 295 (TCC) |
| 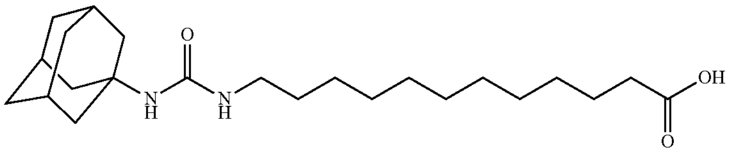 [SMILES: O=C(O)CCCCCCCCCCCNC(=O)NC12CC3CC(CC(C3)C1)C2] | 12-(3-adamantan-1-yl-ureido) dodecanoic acid | 700 (AUDA) |
| 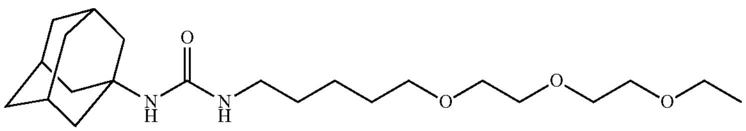 [SMILES: CCOCCOCCOCCCCCNC(=O)NC12CC3CC(CC(C3)C1)C2] | 1-adamantanyl-3-{5-[2-(2-ethoxyethoxy)ethoxy]pentyl]}urea | 950 (AEPU) |
| 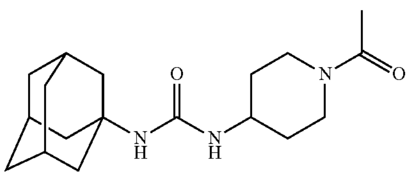 [SMILES: CC(=O)N1CCC(NC(=O)NC23CC4CC(CC(C4)C2)C3)CC1] | 1-(1-acetypiperidin-4-yl)-3-adamantanylurea | 1153 (APAU) |
| 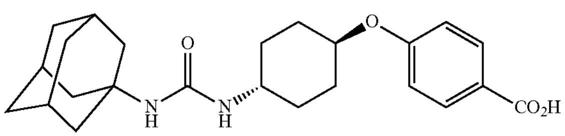 [SMILES: O=C(NC12CC3CC(CC(C3)C1)C2)N[C@H]1CC[C@H](Oc2ccc(C(=O)O)cc2)CC1] | trans-4-[4-(3-Adamantan-1-yl-ureido)-cyclohexyloxy]-benzoic acid | 1471 (tAUCB) |
| 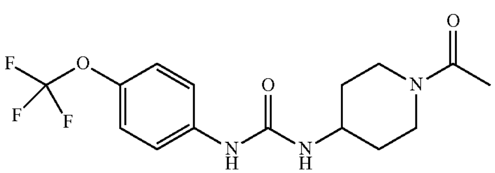 [SMILES: CC(=O)N1CCC(NC(=O)Nc2ccc(OC(F)(F)F)cc2)CC1] | 1-trifluoromethoxyphenyl-3-(1-acetylpiperidin-4-yl) urea | 1555 (TPAU) |

TABLE 2-continued sEH inhibitors

| Structure | Name | sEHi # |
|---|---|---|
| | cis-4-{4-(3-Adamantan-1-yl-ureido)-cyclohexyloxy]-benzoic acid | 1686 (cAUCB) |
| 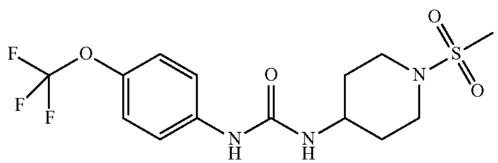 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 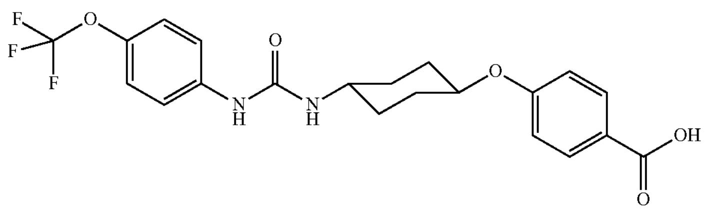 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| 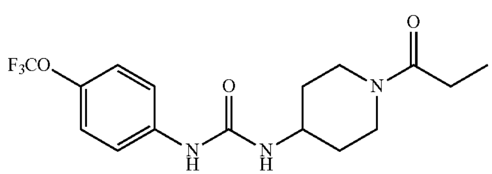 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 (TPPU) |
| 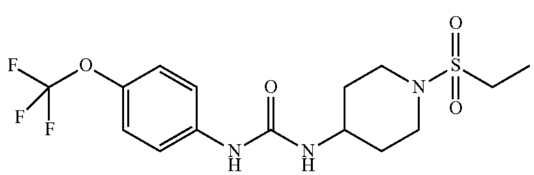 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |

TABLE 2-continued sEH inhibitors

| Structure | Name | sEH # |
|---|---|---|
| 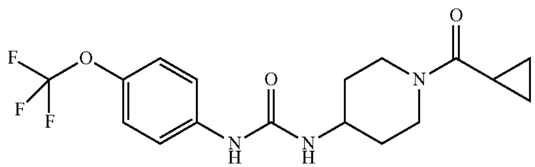 [SMILES: O=C(Nc1ccc(OC(F)(F)F)cc1)NC1CCN(C(=O)C2CC2)CC1] | 1-(1-(cyclopropanecarbonyl)piperidin-4-yl)-3-(4-(trifluoromethoxy)phenyl)urea | 2214 (CPTU) |
| 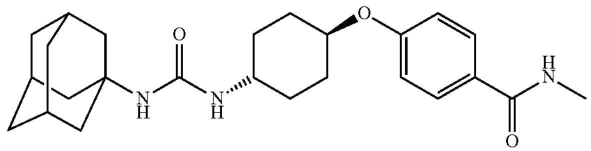 | trans-N-methyl-4-[4-(3-Adamantan-1-yl-ureido)-cyclohexyloxy]-benzamide | 2225 (tMAUCB) |
| 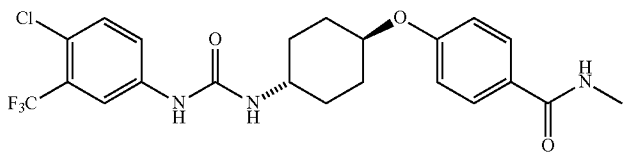 | trans-N-methyl-4-[4-((3-trifluoromethyl-4-chlorophenyl)-ureido)-cyclohexyloxy]-benzamide | 2226 (tMTCUCB) |
| 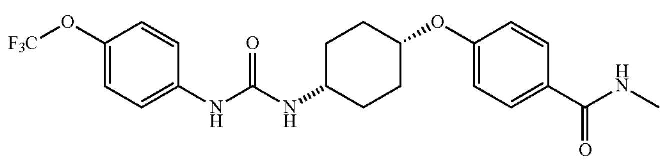 | cis-N-methyl-4-{4-[3-(4-trifluoromethoxy-phenyl)-ureido]-cyclohexyloxy}-benzamide | 2228 (cMTUCB) |
| 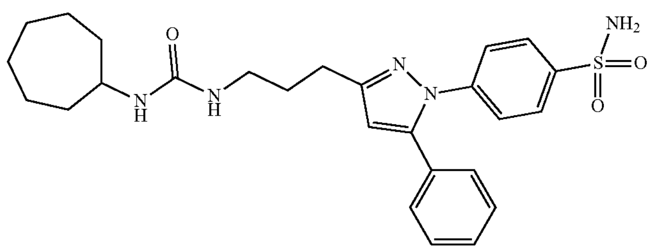 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are described in published International Application Nos PCT/US2015/023048, PCT/US2013/024396, PCT/US2012/025074, PCT/US2011/064474, PCT/US2011/022901, PCT/US2008/072199, PCT/US2007/006412, PCT/US2005/038282, PCT/US2005/08765, PCT/US2004/010298; U.S. Published Patent Application Publication Nos: 2016/0200683, 2015/0011586, 2014/0088156, 2014/0038923, 2013/0274476, 2013/0143925, 2013/0137726, 2011/0098322, 2005/0026844, and U.S. Pat. No. 9,850,207, each of which is hereby incorporated herein by reference in its entirety for all purposes.

A further inhibitor of soluble epoxide hydrolase useful in the present methods is GSK2256294A (IUPAC/Chemical Name: (1R,3S)-N-(4-cyano-2-(trifluoromethyl) benzyl)-3-((4-methyl-6-(methylamino)-1,3,5-triazin-2-yl)amino)cyclohexane-1-carboxamide; CAS#: 1142090-23-0), described in Podolin, et al., *Prostaglandins Other Lipid Mediat.* (2013) 104-105:25-31, the structure of which is provided below:

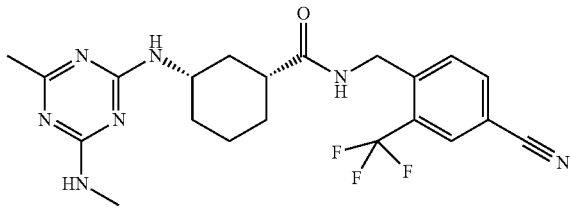 [SMILES: CNc1nc(C)nc(N[C@H]2CCC[C@@H](C(=O)NCc3ccc(C#N)cc3C(F)(F)F)C2)n1]

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S,S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. Nos. 6,150,415 (the '415 patent) and 6,531,506 (the '506 patent).

Derivatives of the sEHI can be designed. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (*Goodman and Gilman's The Pharmacological Basis of Therapeutics*, 13th Edition, 2017, McGraw-Hill). Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, J. Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are contemplated, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, the inhibitor inhibits sEH without also significantly inhibiting microsomal epoxide hydrolase ("mEH"). In various embodiments, at concentrations of 100 µM, the inhibitor inhibits sEH activity by at least 50% while not inhibiting mEH activity by more than 10%. Compounds have an $IC_{50}$ (inhibition potency or, by definition, the concentration of inhibitor which reduces enzyme activity by 50%) of less than about 100 µM. Inhibitors with $IC_{50}$s of less than 100 µM are of use, e.g., compounds with $IC_{50}$s of less than 75 µM e.g., compounds with an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

The sEH inhibitors can be one of several pharmacophores in a molecule. For example, in various embodiments, a compound with combined functionality to concurrently inhibit sEH and COX-2 is exposed to the stem cells in vitro or co-administered with the stem cells in vivo. Urea-containing pyrazoles that function as dual inhibitors of cyclooxygenase-2 and soluble epoxide hydrolase are described, e.g., in Hwang, et al., *J Med Chem.* (2011) 28;54(8):3037-50; WO 2012/082647 and U.S. Pat. No. 9,096,532.

general structure may have different functional groups on:
X: $MeSO_2$ or $H_2NSO_2$
A: various carbon linkers
R: carbocyclic, aryl groups, or heterocylic groups Inhibitory activities against sEH, COX-1 and COX-2 of illustrative dual inhibitors of COX-2 and sEH are provided in Table 3 below.

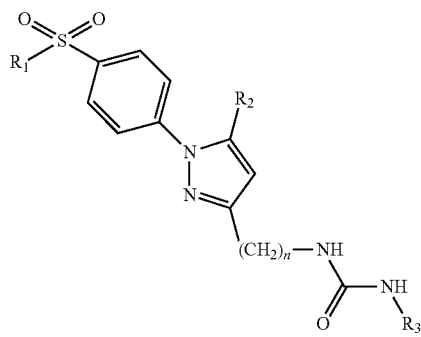

TABLE 3

Inhibitory activities against sEH, COX-1 and COX-2.

| sEH-COX-2 dual inhibitor | $R_1$ | $R_2$ | $R_3$ | n | COX-2 (μM) | COX-1 (% inhibition at 100 mM) | sEH (nM) |
|---|---|---|---|---|---|---|---|
| 1860 | Me | Ph | Adamantyl | 1 | >10 | 12.7 | 25 ± 1 |
| 2321 | Me | Ph | cHep | 1 | >10 | 3.4 | 2.6 ± 0.3 |
| 2322 | Me | Ph | Ph | 1 | >10 | 9.9 | 47 ± 4 |
| 2323 | Me | Ph | p-$CF_3O$—Ph | 1 | 7 | 10.4 | 6.0 ± 0.5 |
| 2324 | Me | Ph | p-$CF_3$—Ph | 1 | >10 | 10.7 | 110 ± 5 |
| 1861 | Me | Ph | m-$CF_3$—Ph | 1 | 2.5 | 7.8 | 72 ± 8 |
| 2107 | $NH_2$ | Ph | m-$CF_3$—Ph | 1 | 1 | 16.9 | 84 ± 6 |
| 2106 | Me | t-butyl | m-$CF_3$—Ph | 1 | >10 | 2.4 | 32 ± 3 |
| 2121 | $NH_2$ | Ph | m-$CF_3$—Ph | 0 | 2 | 33.9 | 88 ± 5 |
| 2313 | $NH_2$ | Ph | m-$CF_3$—Ph | 2 | 1 | 22.0 | 26 ± 3 |
| 1862 | Me | Ph | m-$CF_3$—Ph | 3 | 3 | 6.4 | 3.4 ± 0.2 |
| 2246 | $NH_2$ | Ph | m-$CF_3$—Ph | 3 | 0.71 | 27.2 | 4.1 ± 0.4 |
| 2152 | $NH_2$ | p-Me—Ph | m-$CF_3$—Ph | 3 | 2.8 | 12.1 | 10 ± 1 |
| 2325 | $NH_2$ | Ph | 2,6-diMe—Ph | 3 | >10 | 6.2 | 1550 ± 70 |
| 2245 | $NH_2$ | Ph | Ph | 3 | >10 | 15.8 | 0.8 ± 0.1 |
| 2326 | $NH_2$ | Ph | 1-Adamantyl | 3 | 7 | 6.7 | 0.5 ± 0.1 |
| 2247 | $NH_2$ | Ph | c-Hep | 3 | 2 | 10.2 | 0.5 ± 0.1 |
| 2327 | $NH_2$ | Ph | p-Cl—Ph | 3 | 6 | 15.2 | 0.8 ± 0.1 |
| 2328 (SHH07009A) | $NH_2$ | Ph | p-$CF_3$—Ph | 3 | 1.26 | 22.7 | 0.9 ± 0.1 |
| 2329 (SHH07009B) | $NH_2$ | Ph | p-$CF_3O$—Ph | 3 | 0.92 | 13.8 | 0.5 ± 0.1 |

A general structure of inhibitors that inhibit both COX-2 and sEH are provided below.

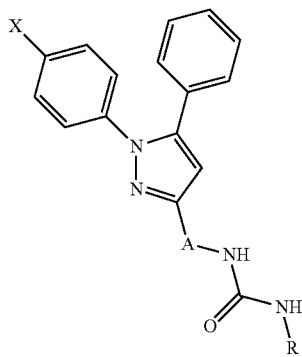

In some embodiments, the dual inhibitor of sEH and COX 2 is a compound in Table 3 selected from the group consisting of:

compound 1860 (1-Adamantan-1-yl-3-[1-(4-methanesulfonyl-phenyl)-5-phenyl-1H-pyrazol-3-ylmethyl]-urea), compound 2321 (1-Cycloheptyl-3-[1-(4-methanesulfonyl-phenyl)-5-phenyl-1H-pyrazol-3-ylmethyl]-urea), compound 2322 (1-[1-(4-Methanesulfonyl-phenyl)-5-phenyl-1H-pyrazol-3-ylmethyl]-3-phenyl-urea), compound 2323 (1-[1-(4-Methanesulfonyl-phenyl)-5-phenyl-1H-pyrazol-3-ylmethyl]-3-(4-trifluoromethoxy-phenyl)-urea), compound 2324 (1-[1-(4-Methanesulfonyl-phenyl)-5-phenyl-1H-pyrazol-3-ylmethyl]-3-(4-trifluoromethyl-phenyl)-urea), compound 1861 (1-[1-(4-Methanesulfonyl-phenyl)-5-phenyl-1H-pyrazol-3-ylmethyl]-3-(3-trifluoromethyl-phenyl)-urea), compound 2107 (4-{5-Phenyl-3-[3-(3-trifluoromethyl-phenyl)-ureidomethyl]-pyrazol-1-yl}-benzenesulfonamide), compound 2106 (1-[5-tert-Butyl-1-(4-methanesulfonyl-phenyl)-1H-pyrazol-3-ylmethyl]-3-(3-trifluoromethyl-phenyl)-urea), compound 2121 (4-{5-Phenyl-3-[3-(3-trifluoromethyl-phenyl)-ureido]-pyrazol-1-yl}-benzenesulfonamide), compound 2313 (4-(5-Phenyl-3-{2-[3-(3-trifluoromethyl-phenyl)-ureido]-ethyl}-pyrazol-1-yl)-benzenesulfonamide), compound 1862 (1-{3-[1-(4-Methanesulfonyl-phenyl)-5-phenyl-1H-pyrazol-3-yl]-propyl}-3-(3-trifluoromethyl-phenyl)-urea), compound 2246 (4-(5-Phenyl-3-{3-[3-(3-trifluoromethyl-phenyl)-ureido]-propyl}-pyrazol-1-yl)-benzenesulfonamide), compound 2152 (4-(5-p-Tolyl-3-{3-[3-(3-trifluoromethyl-phenyl)-ureido]-propyl}-pyrazol-1-yl)-benzenesulfonamide), compound 2325 (4-(3-{3-[3-(2,6-Diisopropyl-phenyl)-ureido]-propyl}-5-phenyl-pyrazol-1-yl)-benzenesulfonamide), compound 2245 (4-{5-Phenyl-3-[3-(3-phenyl-ureido)-propyl]-pyrazol-1-yl}-benzenesulfonamide), compound 2326 (4-{3-[3-(3-Adamantan-1-yl-ureido)-propyl]-5-phenyl-pyrazol-1-yl}-benzenesulfonamide), compound 2247 (4-{3-[3-(3-Cycloheptyl-ureido)-propyl]-5-phenyl-pyrazol-1-yl}-benzenesulfonamide), compound 2327 (4-(3-{3-[3-(4-Chloro-phenyl)-ureido]-propyl}-5-phenyl-pyrazol-1-yl)-benzenesulfonamide), compound 2328 (4-(5-Phenyl-3-{3-[3-(4-trifluoromethyl-phenyl)-ureido]-propyl}-pyrazol-1-yl)-benzenesulfonamide); and compound 2329 (4-(5-Phenyl-3-{3-[3-(4-trifluoromethoxy-phenyl)-ureido]-propyl}-pyrazol-1-yl)-benzenesulfonamide).

Compounds with combined functionality to concurrently inhibit sEH and LOX also find use. Compounds which are combined sEH inhibitors and PPAR agonists also find use.

Preferably, the inhibitor inhibits sEH without also significantly inhibiting microsomal epoxide hydrolase ("mEH"). Preferably, at concentrations of 100 µM, the inhibitor inhibits sEH activity by at least 50% while not inhibiting mEH activity by more than 10%. Preferred compounds have an ICso (inhibition potency or, by definition, the concentration of inhibitor which reduces enzyme activity by 50%) of less than about 100 µM. Inhibitors with $IC_{50}$s of less than 100 µM are preferred, with $IC_{50}$s of less than 75 µM being more preferred and, in order of increasing preference, an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less, being still more preferred. Assays for determining sEH activity are known in the art and described elsewhere herein. The ICso determination of the inhibitor can be made with respect to an sEH enzyme from the species subject to treatment (e.g., the subject receiving the inhibitor of sEH).

c. Inhibitors of COX and/or LOX

The agent that inhibits sEH is co-administered with an agent that preferentially or selectively inhibits COX and/or LOX. When co-administered as separate agents (rather than administered as a dual inhibitor), the agent that inhibits sEH and the agent that inhibits COX-2 can be administered via the same or different routes of administration.

Current non-steroidal anti-inflammatory drugs (NSAIDs) inhibit both isoforms, but most tend to inhibit the two isoforms to different degrees. Since COX-2 is considered the enzyme associated with an inflammatory response, enzyme selectivity is generally measured in terms of specificity for COX-2. Typically, cells of a target organ that express COX-1 or COX-2 are exposed to increasing levels of NSAIDs. If the cell does not normally produce COX-2, COX-2 is induced by a stimulant, usually bacterial lipopolysaccharide (LPS).

The relative activity of NSAIDs on COX-1 and COX-2 is expressed by the ratio of $IC_{50}$s for each enzyme: COX-2 ($IC_{50}$)/COX-1 ($IC_{50}$). The smaller the ratio, the more specific the NSAID is for COX-2. For example, various NSAIDs have been reported to have ratios of COX-2 ($IC_{50}$)/COX-1 ($IC_{50}$) ranging from 0.33 to 122. See, Englehart et al., J Inflammatory Res 44:422-33 (1995). Aspirin has an $IC_{50}$ ratio of 0.32, indicating that it inhibits COX-1 more than COX-2, while indomethacin is considered a COX-2 inhibitor since its COX-2 ($IC_{50}$)/COX-1 ($IC_{50}$) ratio is 33. Even selective COX-2 inhibitors retain some COX-1 inhibition at therapeutic levels obtained in vivo. Cryer and Feldman, Am J Med. 104(5):413-21 (1998).

Commercially available NSAIDs that find use in the methods and compositions of the invention include the traditional NSAIDs diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, the selective COX-2 inhibitors celecoxib, rofecoxib, and valdecoxib, the acetylated salicylates, such as aspirin, and the non-acetylated salicylates, such as magnesium salicylate, choline salicylate, salsalate, salicylic acid esters and sodium salicylate.

d. Inhibitors of 5-LOX

Metabolism of arachidonic acid through the lipoxygenase ("LOX") pathway lead to the formation of leukotrienes ("LTs") that are implicated in a range of pathologies. The primary inflammatory enzyme is 5-lipoxygenase ("5-LOX"). The 5-LOX cascade results in the formation of LTB4 and the cysteinyl LTs LTC4, LTD4, and LTE4. LTB4 is a potent stimulator of leukocyte activation. Cysteinyl LTs "may participate in the damage of gastric mucosa by inducing mucosal microvascular injury and gastric vessel vasoconstriction, promoting breakdown of the mucosal barrier and stimulating the secretion of gastric acid, as well as the production of interleukin 1 ("IL1") and proinflammatory cytokines." Martel-Pelletier et al., Ann. Rheumatic Dis 62:501-509 (2003) ("Martel-Pelletier 2003"). Additional lipoxygenases, 12-LOX and 15-LOX, exist that contribute to the formation of anti-inflammatory compounds known as lipoxins, or LXs. Thus, for purposes of reducing inflammation, it is desirable to inhibit 5-LOX without also inhibiting 12-LOX and 15-LOX.

Because of its role in inflammation, a number of inhibitors of 5-LOX have been developed. See, e.g., Julemont et al., Expert Opinion on Therapeutic Patents, 13(1):1-13 (2003) (review of patents directed to 5-LOX inhibitors for 1999-2002). One orally effective inhibitor is REV 5901 [alpha-pentyl-3-(2-quinolinylmethoxy)-benzene-methanol](see, Van Inwegen et al., Pharmacol Exp Therapeutics 241(1): 117-124 (1987)). 5-LOX can also be inhibited by inhibiting the 5-lipoxygenase activating protein ("FLAP") by MK-886. (see, Smirnov et al., Br J Pharmacol 124:572-578 (1998)). This inhibitor, however, induces apoptosis in some cell types and is best used in in vitro studies. Other inhibitors are described in, e.g., U.S. Patent Application No. 20040198768 e. Joint COX/LOX Inhibitors

Because of the inflammatory effects of prostaglandins and leukotrienes, and because blocking the COX pathway has been thought to shuttle arachidonic acid into the LOX pathway, it has been suggested that dual inhibition of both COX-2 and 5-LOX would maximize the inhibition of inflammation. See, e.g., Martel-Pelletier 2003, supra. Several compounds have been developed to block both COX-2 and 5-LOX. One, tepoxalin, blocks COX-1, COX-2, and 5-LOX, and is commercially available as a veterinary pharmaceutical for dogs, under the name Zubrin® (Schering Plough Animal Health Corp., Union, N.J.). Tepoxalin has also been shown to block the COX enzymes and LOX in humans and to be well tolerated. A second inhibitor of COX and 5-LOX, licofelone (Merkle GmbH, Germany), is in Phase III clinical trials as a treatment for osteoarthritis and has shown gastric tolerability superior to naproxen. See, Bias et al., Am J Gastroenterol 99(4):611 (2004). See also, Martel-Pelletier 2003, supra; Tries et al., Inflamm Res 51:135-43 (2002). A number of other dual COX/LOX inhibitors, and especially COX-2/5-LOX inhibitors, have been developed, as exemplified by U.S. Pat. No. 6,753,344 (thiophene substituted hydroxamic acid derivatives), U.S. Pat. No. 6,696,477 (heterocyclo substituted hydroxamic acid derivatives), U.S. Pat. No. 6,677,364 (substituted sulfonylphenylheterocycles), and U.S. Patent Application Nos. 20040248943 (pyrazole substituted hydroxamic acid derivatives), 20040147565 (substituted sulfonylphenylheterocycles), 20030180402 (flavans isolated from the genus *Acacia*), and 20030176708 (thiophene substituted hydroxamic acid derivatives).

6. Formulation and Administration

The agents for administration in the present methods (e.g., one or more chemotherapeutic agents, e.g., a platinum coordination complex agent and/or a pyrimidine analog, in combination with an inhibitor of sEH, an inhibitor of COX-2 or a dual sEH/COX-2 inhibitor) can be formulated and administered together (e.g., as a mixture) or separately. In some embodiments, the agents are administered via the same or different routes of administration. In some embodiments, the agents are co-administered concurrently or sequentially. The different pharmacologically active agents can be prepared and administered in a wide variety of oral, parenteral and topical dosage forms. In some embodiments, e.g., depending on the cancer being treated and other considerations, the agents can be administered together or separately orally, by injection, that is, intravenously, intramuscularly, intracutaneously, subcutaneously, intraduodenally, intravesically, intraperitoneally or intratumorally. The one or more agents can also be administered by inhalation, for example, intranasally or intrapulmonarily. Additionally, the one or more agents can be administered transdermally. Accordingly, in some embodiments, the one or more active agents are co-administered formulated in a pharmaceutically acceptable carrier or excipient.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of co-inhibition of sEH and COX-2 by replacing the active ingredient or ingredient with an inhibitor of sEH and an inhibitor of COX-2 or a dual sEH/COX-2 inhibitor. It is presumed that the person of skill is familiar with these various vehicles and preparations and they need not be described in detail herein.

The one or more pharmacologically active agents can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the one or more active agents are formulated in a cream. Typically, the cream comprises one or more hydrophobic lipids, with other agents to improve the "feel" of the cream or to provide other useful characteristics. In one embodiment, for example, a cream of the invention may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In the studies reported in the Examples, sEHI were mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the one or more active agents are formulated in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents are administered (that is, whether by lotion, gel, spray, etc.), they are preferably administered at a dosage of about 0.01 mg to 10 mg per 10 cm$^2$.

In some embodiments, the one or more active agents can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

Because the one or more chemotherapeutic agents (e.g., a platinum coordination complex and/or a pyrimidine analog), can function in a cooperative or synergistic manner with an agent or agents for co-inhibition of sEH and COX-2, when co-administered, the one or more active agents can be administered in a reduced dosage or sub-therapeutic amount relative to the dose or amount needed for an efficacious response if the active agent were administered alone. The dosage of the specific compounds depends on many factors that are well known to those skilled in the art. They include for example, the route of administration and the potency of the particular compound. An exemplary dose of a dual sEH/COX inhibitor is from about 0.1 mg/kg to about 10 mg/kg, 25 mg/kg, 50 mg/kg, 100 mg/kg, 150 mg/kg, 200 mg/kg, 250 mg/kg, 300 mg/kg, 350 mg/kg, 400 mg/kg, or 500 mg/kg body weight of the mammal. Doses of anti-inflammatory agents (e.g., NSAIDs, including inhibitors of COX-1, COX-2 and/or 5-LOX) and chemotherapeutic agents are known in the art, and can be found, e.g., in the published literature and in reference texts, e.g., the Physicians' Desk Reference, 71st Ed., 2017, PDR Network, or Brunton and Knollmann, Goodman & Gilman's The Pharmacological Basis of Therapeutics, 13th edition, 2017, McGraw-Hill Education/Medical).

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics*, 13th Edition, 2017, supra; in a Physicians' Desk Reference (PDR), 71st Edition, 2017 (PDR Network); in *Remington: The Science and Practice of Pharmacy*, 21st Ed., 2005, supra; and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference.

In some embodiments, the one or more agents can be provided with a so-called "enteric" coating, such as those used for some brands of aspirin, or embedded in a formulation. Such enteric coatings and formulations are well known in the art. In some formulations, the compositions of the invention are embedded in a slow-release formulation to facilitate administration of the agents over time.

It is understood that the pharmacologically active agents have half-lives defined by the rate at which they are metabolized by or excreted from the body, and that the agents will have a period following administration during which they will be present in amounts sufficient to be effective (either acting alone or in cooperation). It is desirable that the one or more agents be administered during the period during which the other cooperating agents are also present in amounts to be efficacious. In some embodiments, the co-inhibitor(s) of sEH and COX-2 are administered within (e.g., before or after) 72, 60, 48, 36, 24, 12, 10, 8, 6, 4, 2, hours, 1 hour, or one half hour before or after administration of the one or more chemotherapeutic agents (e.g., a platinum coordination complex chemotherapy agent and/or a pyrimidine analog).

7. Methods of Monitoring

A variety of methods can be employed in determining the efficacy of co-inhibition of sEH and COX-2 in potentiating the anticancer effects of a chemotherapy regime comprising one or more chemotherapeutic agents (e.g., a platinum coordination complex and/or a pyrimidine analog). Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. Co-inhibition of sEH and COX-2 in combination with a chemotherapeutic regime comprising one or more chemotherapeutic agents (e.g., a platinum coordination complex and/or a pyrimidine analog), can be screened for prophylactic or therapeutic efficacy in animal models, e.g., in comparison with untreated or placebo controls. Co-inhibition of sEH and COX-2 in combination with a chemotherapeutic regime comprising one or more chemotherapeutic agents (e.g., a platinum coordination complex and/or a pyrimidine analog), can be analyzed for the capacity to reduce or inhibit tumor growth, promote tumor regression, prevent or delay metastasis, and/or prolong survival. For example, multiple dilutions of sera can be tested on tumor cell lines in culture and standard methods for examining cell death or inhibition of cellular growth can be employed. (See, e.g., Green and Sambrook, *Molecular Cloning: A Laboratory Manual*, 4$^{th}$ Edition, Cold Spring Harbor Lab., New York, 2012; Ausubel, et al. Editor, *Current Protocols in Molecular Biology*, USA, 1984-2017; and Bonifacino, et al., Editor, *Current Protocols in Cell Biology*, USA, 2010; all of which are incorporated herein by reference in their entirety.)

The present methods provide for detecting inhibition disease in subject suffering from or susceptible to various cancers. A variety of methods can be used to monitor both therapeutic treatment for symptomatic subjects and prophylactic treatment for asymptomatic subjects.

Monitoring methods entail determining a baseline value of a tumor burden in a subject before co-inhibiting sEH and COX-2 in combination with a chemotherapy regime comprising one or more chemotherapeutic agents (e.g., a platinum coordination complex and/or a pyrimidine analog), and comparing this with a value for the tumor burden after treatment, respectively.

With respect to therapies entailing co-inhibiting sEH and COX-2 in combination with a chemotherapy regime comprising one or more chemotherapeutic agents (e.g., a platinum coordination complex and/or a pyrimidine analog), a significant decrease (i.e., greater than the typical margin of experimental error in repeat measurements of the same sample, expressed as one standard deviation from the mean of such measurements) in value of the tumor burden signals a positive treatment outcome (i.e., that co-inhibiting sEH and COX-2 in combination with a chemotherapy regime comprising one or more chemotherapeutic agents (e.g., a platinum coordination complex and/or a pyrimidine analog), has blocked or inhibited, or reduced progression of tumor growth and/or metastasis).

In other methods, a control value of tumor burden (e.g., a mean and standard deviation) is determined from a control population of individuals who have undergone a chemotherapy regime comprising one or more chemotherapeutic agents (e.g., a platinum coordination complex and/or a pyrimidine analog), in the absence of co-inhibition sEH and COX-2. Measured values of tumor burden in a subject receiving co-inhibition of sEH and COX-2 are compared with the control value. If the measured level in a subject is not significantly different (e.g., more than one standard deviation) from the control value, or is significantly above the control value, treatment can be re-evaluated or discontinued. If the tumor burden level in a subject is significantly below the control value, continued administration of agent is warranted.

In other methods, a subject who is not presently receiving treatment but has undergone a previous course of treatment is monitored for tumor burden to determine whether a resumption of treatment is required. The measured value of tumor burden in the subject can be compared with a value of tumor burden previously achieved in the subject after a previous course of treatment. A significant decrease in tumor burden relative to the previous measurement (i.e., greater than a typical margin of error in repeat measurements of the same sample) is an indication that treatment can be resumed. Alternatively, the value measured in a subject can be compared with a control value (mean plus standard deviation) determined in a population of subjects after undergoing a course of treatment. Alternatively, the measured value in a subject can be compared with a control value in populations of prophylactically treated subjects who remain free of symptoms of disease, or populations of therapeutically treated subjects who show amelioration of disease characteristics. In all of these cases, a significant increase in tumor burden relative to the control level (i.e., more than a standard deviation) is an indicator that treatment should be resumed in a subject.

The tissue sample for analysis is typically blood, plasma, serum, mucous, tissue biopsy, tumor biopsy, ascites or cerebrospinal fluid from the subject. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

8. Kits

Further provided are kits. In some embodiments, the kits comprise vials or containers (including pill blister packaging) of unit doses for administering to a subject a regimen of one or more chemotherapeutic agents (e.g., a platinum coordination complex and/or a pyrimidine analog), an inhibitor of soluble epoxide hydrolase (sEHi) and a non-steroidal anti-inflammatory drug (NSAID) that inhibits one or more enzymes selected from the group consisting of cyclo-oxygenase ("COX")-1, COX-2, and 5-lipoxygenase ("5-LOX"), as described above and herein. In some embodiments, the kits further comprises vials or containers (including pill blister packaging) of unit doses for administering to a subject a pyrimidine analog, e.g., a deoxycytidine analog, as described above and herein.

EXAMPLES

The following examples are offered to illustrate, but not to limit the claimed invention.

Example 1

COX-2/sEH Dual Inhibitor PTUPB Potentiates the Anti-Tumor Efficacy of Cisplatin Materials and Methods Materials and Supplies. Bladder cancer subject-derived xenograft (PDX) models were provided by The Jackson Laboratory (JAX, Bar Harbor, Me.). PDXs were developed through subcutaneous implantation from clinical tumor tissues into immunodeficient NOD.Cg-Prkdcscid Il2rgtm1Wjl/SzJ (NSG; JAX strain #5557) female mice, followed by serial in vivo passaging as previously described (22). All experiments utilized PDX models within the first five passages. Cisplatin was purchased from Fresenius Kabi USA, LLC (Lake Zurich, Ill). Gemcitabine was purchased from LC Laboratories (Woburn, Mass.). [$^{14}$C]carboplatin was purchased from GE Healthcare (Waukesha, Wis.) and was prepared as described (23, 24). Celecoxib was a gift from Pfizer. PTUPB and t-AUCB were synthesized as previously described (21, 24). The bladder cancer cell lines 5637, J82, T24 and TCCSUP were purchased from American Type Culture Collection (ATCC, Manassas, Va.) in 2007 and stored in liquid N2. Cells were thawed and cultured with RPMI-1640 medium supplemented with 10% fetal bovine serum (Gibco, Grand Island, N.Y.) and 1% penicillin-streptomycin (Gibco, Grand Island, N.Y.) and incubated at 37° C. in 5% CO2. The cell lines have not been tested and authenticated by the authors.

PDX bladder cancer. NSG PDX studies were performed at the University of California Davis with IACUC approval. Experiments were carried out with 6 to 9 week old female NSG mice bearing bladder cancer PDX models (UC Davis ID# BL0293 or JAX Model # TM00016; UC Davis ID#BL0269 or JAX Model #TM00015). When tumors achieved volumes of 100~200 mm$^3$, mice were randomized to different treatment groups as follows: vehicle control (PEG 300, 10 mL/kg, oral), PTUPB, cisplatin, t-AUCB, celecoxib, combinations of PTUPB and cisplatin, t-AUCB and cisplatin, celecoxib and cisplatin, gemcitabine and cisplatin (GC), PTUPB and GC. PTUPB (30 mg/kg in PEG 300), celecoxib (30 mg/kg in PEG 300), t-AUCB (3 mg/kg in PEG 300) were administered once per day by oral gavage for up to 30 days. Cisplatin (1 mg/ml) was diluted in 0.9% saline and administered at a dose of 2 mg/kg (IV, tail vein, once per day) on days 1, 2, 3, 15, 16 and 17. Gemcitabine was dissolved in 0.9% saline and administered at a dose of 150 mg/kg (IP, weekly) for 4 weeks. Animal weight and tumor size were measured twice per week. The tumor volume was calculated with the following formula: length (mm)×width (mm)×width (mm)×0.5. The percentage of tumor growth inhibition (TGI) was calculated as follows; $100\% \times (1-[(V^{treated}_{(final\ day)} - V^{treated}_{(initial\ day)})/(V^{control}_{(final\ day)} - V^{control}_{(initial\ day)})])$, where V is tumor volume.

Blood samples from mice were collected and analyzed for complete blood count (CBC), blood urea nitrogen (BUN), aspartate aminotransferase (AST), creatinine and total bilirubin at the Veterinary Medicine Comparative Pathology Laboratory of University of California Davis. The tumor, heart, liver, spleen, lung and kidney were harvested and the tissue samples were fixed in formalin or frozen at −80° C. Tumor sections were stained with hematoxylin and eosin (H&E) or were used for immunohistochemistry analysis. A board-certified pathologist provided detailed interpretation of tumor histomorphology and scoring of immunohistochemical staining. Some of the tumor sections were lysed and chromatographed using SDS-PAGE followed by transfer onto a PVDF membrane. The membranes were blocked in 5% nonfat dry milk for 1 h at room temperature, and probed with p-AKT(S473), p-ERK(Thr202/Tyr204), total-AKT, total-ERK and rabbit monoclonal anti-GAPDH antibodies (Cell Signaling Technology, Beverly, Mass.). The membranes were then probed with horseradish peroxidase (HRP) tagged secondary antibodies and epitopes were detected using the ECL Plus Western Blotting Detection Reagent (GE Healthcare, Piscataway, N.J.). Cell proliferation and apoptosis assessed with Ki-67 and cleaved caspase-3 antibodies (Cell Signaling, Danvers, Mass.) using an immunohistochemistry kit per the manufacturer's instructions (BioGenex, Fremont, Calif.).

Accelerator mass spectrometry to determine platinum-DNA adduct formation. The ATCC 5637 bladder cancer cell line and NSG-PDX mice were used to assess the impact of PTUPB on [$^{14}$C]carboplatin -DNA adduct levels as a surrogate of cisplatin-DNA adducts.

Carboplatin-DNA adduct formation in vitro. For cell culture studies, 60-mm dishes of 5637 cell cultures were either pretreated with 10 µM PTUPB for 5 hr followed by 100 µM [$^{14}$C]carboplatin (36,000 dpm/mL), or simultaneously dosed with PTUPB and [14C]carboplatin. Four hours after carboplatin was added, the cells were washed with PBS. The 4 hr incubation time was chosen due to the in vivo carboplatin half-life (1.3-6 hr) in subjects. Cells were harvested at the 4 hr time point in one group of dishes and another group was washed and further incubated for 20 hr with fresh drug-free medium before cell harvest in order to determine DNA repair. Cell pellets were stored at −80° C. until DNA extraction.

Carboplatin-DNA adduct formation in vivo. NSG PDX mice bearing BL0293 tumors were dosed with 10 µL/g of 37.5 mg/kg [$^{14}$C]carboplatin (50,000 dpm/g) via IV bolus injection. PTUPB (30 mg/kg in PEG 400) was administered via oral gavage 1 hr or 16 hr before carboplatin dosing. Mice were sacrificed and tumor tissues harvested 24 hours after carboplatin dosing. DNA was extracted using a Promega Wizard genomic DNA purification kit according to manufacturer's instructions. Ten micrograms of DNA per sample was submitted to Lawrence Livermore National Laboratory (LLNL) for AMS analysis using previously reported protocol (25).

Median effect analysis to determine in vitro drug-drug interaction. The method published by Chou and Talalay was used to determine the extent and nature (synergism, additivity and antagonism) of PTUPB and cisplatin interaction in cell culture (26, 27). PTUPB was dissolved in dimethyl sulfoxide (DMSO) to a final stock concentration of 10 mM. Cisplatin was dissolved in PBS to a final stock concentration of 10 mM. Cells were seeded at 2,000-3,000 cells and 100 µl of medium per well into 96-well plates (Becton Dickinson, Franklin Lakes, N.J.), and incubated overnight. Different concentrations of these two drugs were diluted in culture media and added to each well. The plates were then incubated for an additional 72 hours. The control group was dosed with 0.2% DMSO. Cell viability assays (MTS) were performed according to the manufacturer's protocol (Promega, Madison, Wis.). The absolute 50% inhibitory concentrations (IC50) were calculated as previously described (28). Dose-response curves were generated with GraphPad Prism 5 software (GraphPad Software Inc., La Jolla, Calif.). The combination indices (CI) were determined based on the method of Chou et al (26). CI values were calculated with CompuSyn software (http://www.combosyn.com/).

Oxylipin profile analysis. Lipid extraction and analysis was performed as previously reported (20). Briefly, for tumor lipid mediator extraction, ~100 mg of tumor tissues was mixed with an antioxidant solution (0.2 mg/mL butylated hydroxytoluene and 0.2 mg/mL triphenylphosphine in methanol), the surrogate solution, and 400 µL of extract solution (0.1% acetic acid with 0.2 mg/mL butylated hydroxytoluene in methanol), and then homogenized. The resulting homogenates were kept overnight at −80° C. Next day, the homogenates were centrifuged and supernatants were collected. The pellets were washed with 0.1% butylated hydroxytoluene and 0.1% acetic acid in methanol and the supernatants were collected and combined. LC-MS/MS analysis of the extracts were carried out on an Agilent 1200SL liquid chromatographic system coupled to a 4000 QTRAP MS/MS instrument (AB Sciex) as described (29).

Statistics. Data are presented as mean±standard error of the mean (SEM) or mean±standard deviation (SD). Group comparisons were carried out using one-way analysis of variance or Student's t test. Survival analysis was performed using the Kaplan-Meier method. A p value of less than 0.05 was considered statistically significant.

Results

Co-administration of PTUPB potentiated the anti-tumor activity of cisplatin. We previously showed PTUPB had anti-tumor activity in mouse Lewis lung cancer (LLC) and NDL (Her2+, Ki67+, ER/PR negative) breast carcinoma models (20). Here, we determined whether PTUPB possessed anti-tumor activity in human bladder cancer cell lines and PDXs, and synergized with cisplatin treatment. We used bladder cancer PDX models BL0293 and BL0269. These tumor types, like most bladder cancers in the clinic, are only moderately sensitive (BL0293) or resistant (BL0269) to cisplatin (22). Treatment with single agent PTUPB or cisplatin exhibited moderate anti-tumor activity in mice bearing BL0293 tumors (FIG. 2). The time required to reach a 7.5 fold increase in tumor volume was used as a reasonably achievable endpoint to evaluate tumor growth among treatment groups. The vehicle only control had a median time to a 7.5-fold increase in tumor volume of 20.0 days, whereas the median times to this endpoint were 24.4 days (p=0.085) and 35.8 days (p=0.0003) for the PTUPB and cisplatin monotherapy groups, respectively. The median time to a 7.5-fold increase in tumor volume in the cisplatin plus PTUPB combination group was significantly longer (60.9 days) than that of either PTUPB (p=0.007) or cisplatin (p=0.02) single agent treatment groups (FIG. 2A). Analysis of overall survival showed that single agent PTUPB did not significantly increase survival time compared to control (39.4 days vs. 31.3 days, p=0.201), whereas single agent cisplatin treatment extended survival to 47.0 days (p=0.004). The survival time could be further significantly increased by co-treatment of mice with PTUPB and cisplatin to 60.9 days, which was longer than that of either the PTUPB (p=0.007) or cisplatin (p=0.02) monotherapy groups (FIG. 2B). In PDX model BL0269, which is resistant to cisplatin and gemcitabine monotherapy (FIG. 2C), tumor growth was significantly inhibited in the PTUPB plus cisplatin combination group (p=0.006). Furthermore, addition of PTUPB to GC resulted in the best inhibition of tumor growth (FIG. 2D). We also performed experiments to examine the efficacy of combination treatments of celecoxib with cisplatin and t-AUCB with cisplatin in bladder PDX model BL0269. We did not observe any potentiation of cisplatin by celecoxib with respect to inhibiting tumor growth, but we observed moderate additive effect of t-AUCB with cisplatin (FIG. 3). PTUPB has the best and most statistically significant potentiation of cisplatin efficacy amongst these treatment groups.

Figure 6:
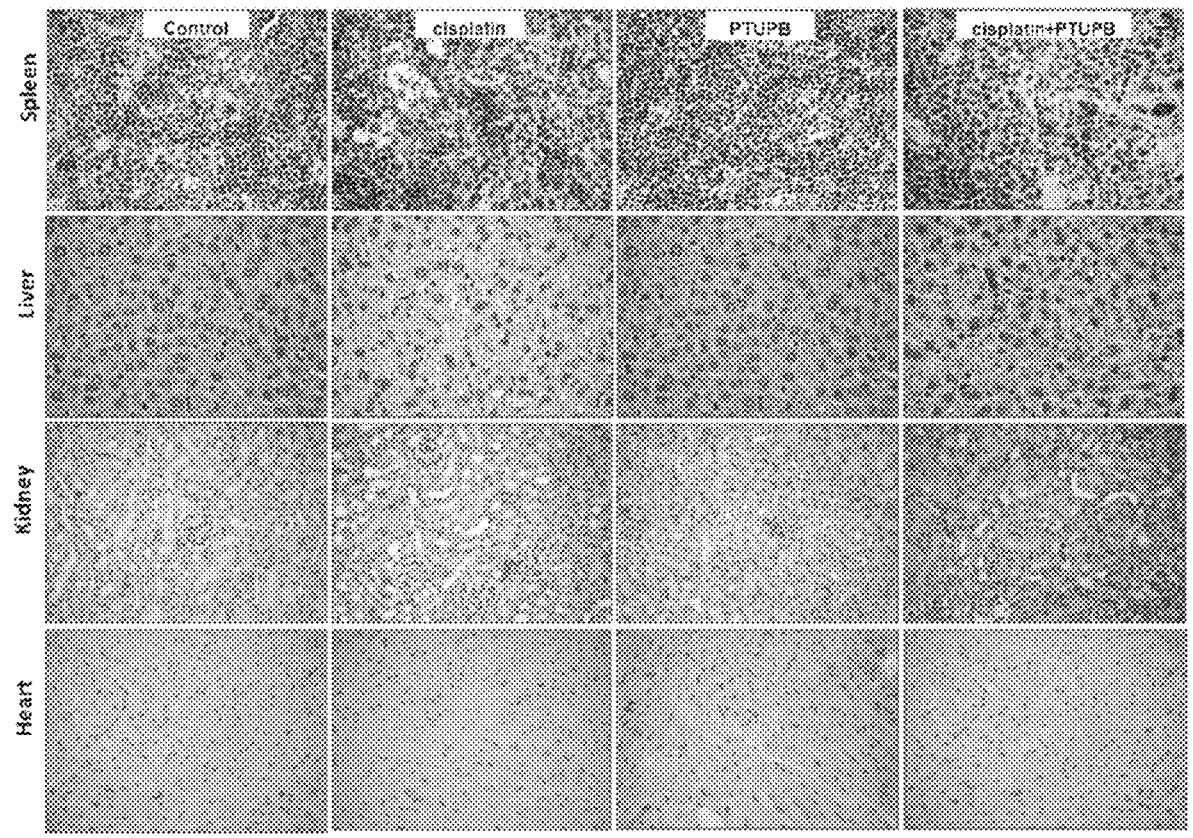
FIG. 6 illustrates Histopathological evaluation of major organs (H&E staining). Cisplatin treatment induced old hemorrhage in the spleen red pulp characterized with focal hemosiderin deposit. The control and PTUPB treatment show no overt histological changes in the spleen red pulp and white pulp architecture. Cisplatin or combined treatment induced cytoplasmic vacuolization (microvesicular steatosis) in the hepatocytes that could be due to normal variations. There is minimal steatosis, mild portal, and lobular inflammation. No overt liver histologic changes were observed. No overt histological damage in the kidney tissue was detected in the control and PTUPB treatment groups. Cisplatin induced distal tubule cells swollen in the combined treatment. No overt histological damage in the heart tissues was caused by cisplatin treatment. These data demonstrated the safety application of COX-2/sEH dual inhibitor PTUPB plus cisplatin therapy in bladder cancer treatment.

Even though PTUPB potentiated the anti-tumor efficacy of cisplatin, we did not observe any significant increase in toxicity. In the BL0293 model, compared to vehicle control, PTUPB monotherapy slightly decreased body weight (p=0.086 at day 23; p=0.118 at day 30) while cisplatin treatment led to significant weight loss (p<0.001 at day 23; p=0.008 at day 30). The addition of PTUPB to cisplatin therapy did not further increase weight loss (FIG. 4A). We did not observe any significant weight loss in the BL0269 groups, regardless of the treatment (FIGS. 4B, 4C). We also determined complete blood cell count (CBC) and chemistry panels at days 6 and 20 of treatment (FIG. 5). No significant difference in blood panel data was observed among all treatment groups compared to the controls. Histology examination of major organs at day 20 revealed cisplatin and combination treatment induced swollen distal tubule cells in kidneys, and cytoplasmic vacuolization (microvesicular steatosis) in hepatocytes. Although these changes were consistent with cisplatin toxicity, they were modest and could be due to normal variations in tissue morphology. However, no such morphology changes were observed in the control and PTUPB monotherapy groups, suggesting that the changes were caused by cisplatin. No other histological changes were observed in other organs (FIG. 6).

Figure 7:
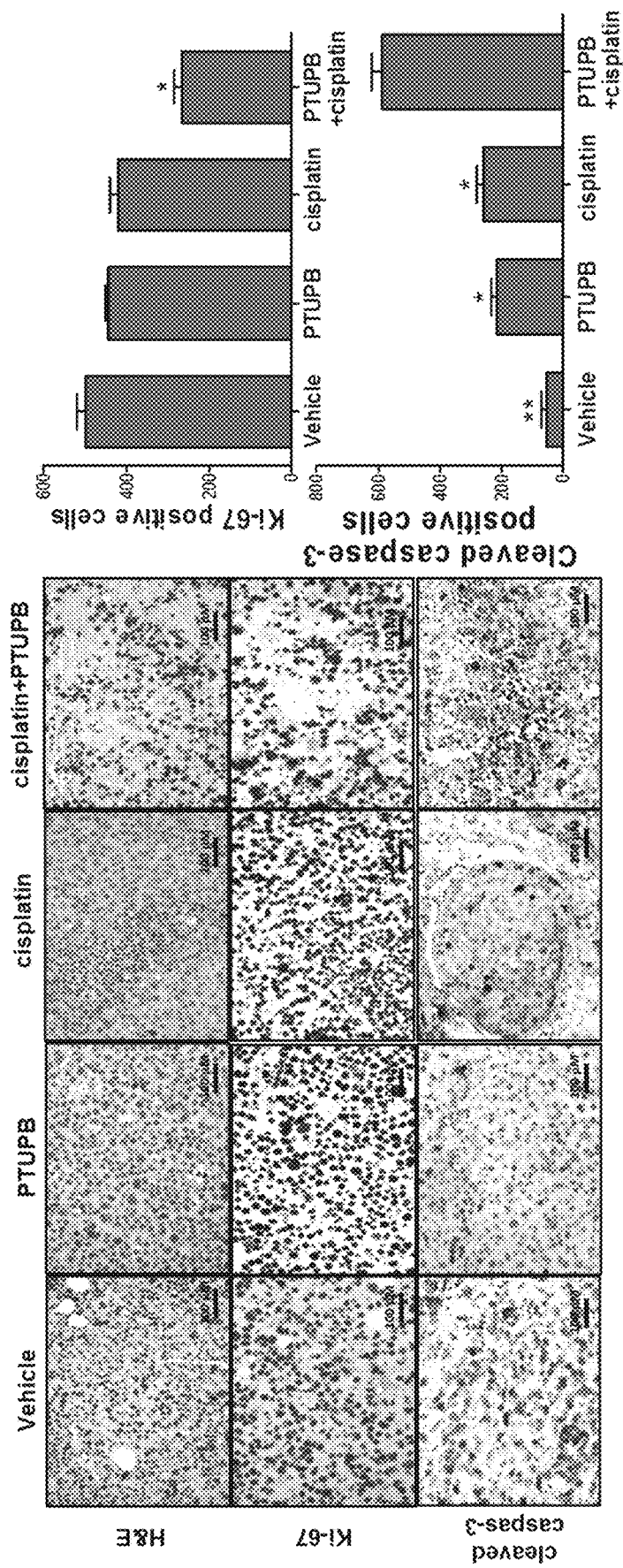
FIG. 7 illustrates that cisplatin plus PTUPB decreases proliferation and increases apoptosis markers. Ki-67 and caspase-3 expression as determined by immunohistochemical (IHC) analysis. Formalin-fixed paraffin-embedded xenograft sections were stained for H&E, Ki-67 and caspase-3. Top panel: Hematoxylin and Eosin stain (H & E stain). Middle panel: Ki-67 staining. More Ki-67 positive cells were observed in the control group, but significantly decreased in the combination group. Bottom Panel: cleaved caspase-3. Compared with the control group, increasing numbers of cells stained positive for cleaved caspase-3 in the PTUPB plus cisplatin combination group. Quantitative data of Ki67 and cleaved caspase-3 staining in each group were generated from randomly selected 20 fields and are shown along with the images. *: p<0.05.
Figure 8:
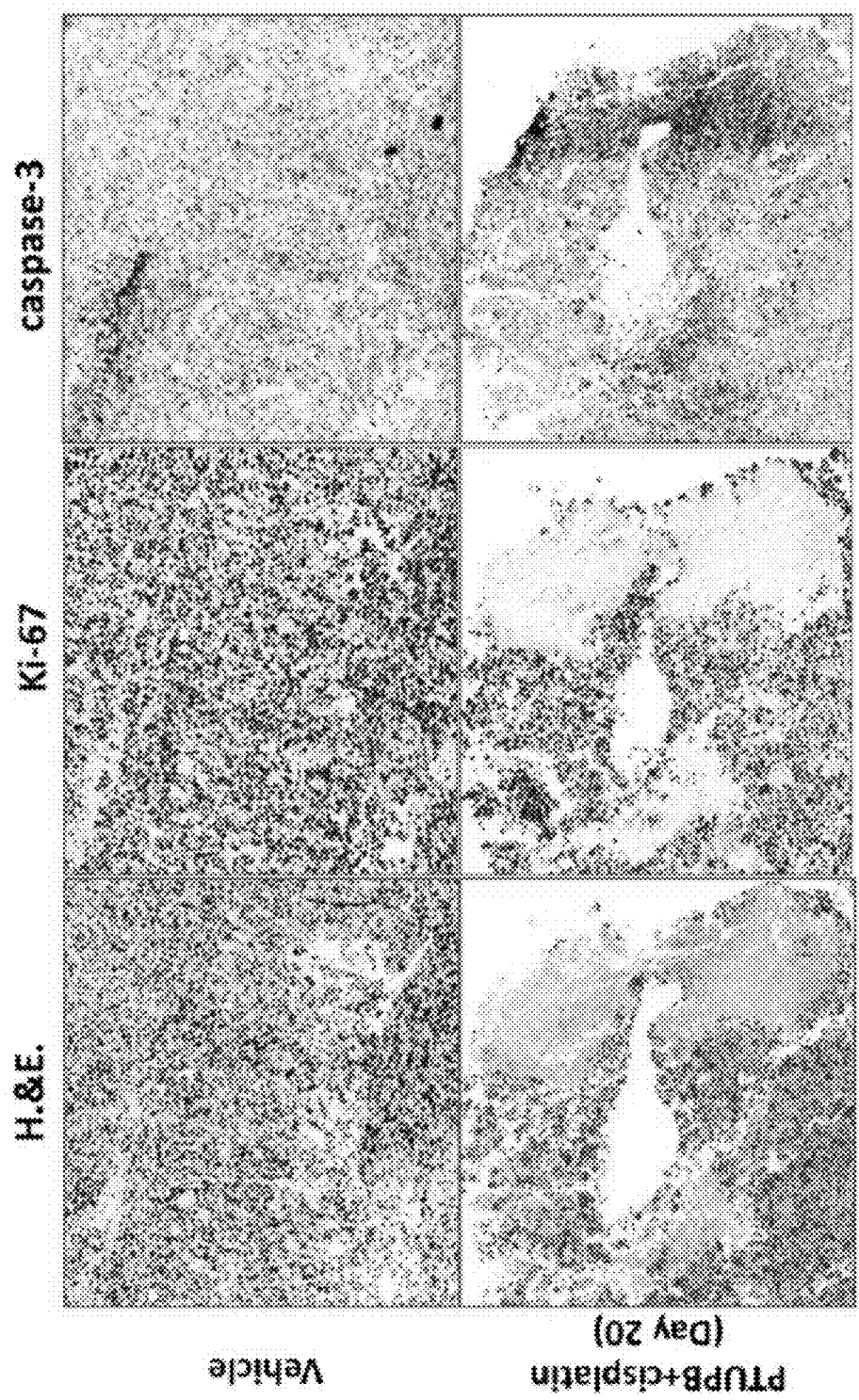
FIG. 8 illustrates IHC staining of bladder PDX tumor tissues (BL0293). Left panel: Comparison of morphology between the control and PTUPB groups in BL0293 PDX model. Hematoxylin and eosin stain (H & E stain) showed that more tumor cells in control group compared to the PTUPB plus cisplatin-treated mice. Similarly, more Ki67 positive cells were observed in the control group (middle panel), suggesting more cells were in cell proliferation. Right Panel: Staining of Cleaved Caspase 3. Compared with the control group, increasing numbers of cells stained positive for active caspase-3 in the PTUPB plus Cisplatin group indicating the progression of apoptosis across the cell population.

Combination treatment of cisplatin and PTUPB inhibited proliferation and induced apoptosis in bladder cancer PDX. Ki-67 is a nuclear non-histone protein that is preferentially expressed in dividing cells, and is frequently used to assess the proliferation state of tissues. The determination of cleaved caspase 3 is commonly used as an indicator of apoptosis. The combination of cisplatin with PTUPB treatment led to a significant decrease of Ki-67 expression and substantial increase of cleaved caspase-3 in stained tumor tissues when compared to single treatment with PTUPB or cisplatin (FIG. 7 and FIG. 8). These data demonstrate that the anti-tumor activity of the combination treatment with PTUPB and cisplatin was, at least in part, due to decreased cell proliferation and increased apoptosis.

Combination treatment of cisplatin and PTUPB significantly reduced the activity of signaling pathways essential for cell growth. The MAPK/ERK and PI3K/AKT/mTOR signaling pathways are shared by many receptor tyrosine kinases and often essential for tumor growth and survival. To determine how the different treatments affected these two signaling pathways, tumor tissues were collected at day 3 after treatment started, and at day 17 when tumors started to regrow in the PTUPB and cisplatin groups or were stabilized as in the combination group. While treatment with either PTUPB alone or cisplatin alone did not significantly diminish levels of either phosphorylated activated ERK (p-ERK) or AKT (p-AKT), the combination treatment of PTUPB and cisplatin substantially decreased levels of both p-ERK and p-AKT at day 3. On Day 17, increased levels of p-ERK and p-AKT were observed in the PTUPB and cisplatin combination group (FIG. 9). These data confirmed that combined therapy suppressed bladder cancer growth, at least in part, through these two pathways, while pathway reactivation was associated with tumor adaptation and re-growth.

PTUPB did not alter platinum DNA adduct formation. As alkylating agents, platinum-based drugs (including cisplatin and carboplatin) kill cancer cells through formation of covalent drug-DNA adducts. We determined whether PTUPB potentiated the anti-tumor activity of platinum agents via increasing DNA adducts by using [$^{14}$C]carboplatin-DNA adducts as a surrogate marker that is amenable to AMS analysis. AMS is ultrasensitive for quantification of $^{14}$C in biological sample, and was used to measure carboplatin-DNA adduct formation under physiologically relevant drug concentrations (30). Since cisplatin does not have any carbon atoms in the molecule, it cannot be labeled with $^{14}$C. Since both cisplatin and carboplatin form the same therapeutically relevant drug-DNA diadducts and share a similar resistance spectrum (31), we used [$^{14}$C]carboplatin for this part of the study.

First, we determined the effect of PTUPB on carboplatin-DNA adduct formation in cell culture with the bladder cancer cell line 5637 (32). Cultures of 5637 cells were treated with either carboplatin (100 µM) alone or a combination of carboplatin (100 µM) and PTUPB (10 µM). The 100 µM concentration of carboplatin was used based on its maximum blood concentration in subjects after chemotherapy and the treatment duration of 4 hours was chosen to simulate carboplatin plasma half-life of 1.5-6.0 hours in subjects. PTUPB exposure did not significantly alter platinum-DNA adduct formation after 4h (528±41 adducts per $10^8$ nt with the carboplatin alone versus 593±282 adducts per $10^8$ nt with the combination treatment, p=0.713) (FIG. 10A). Similarly, pretreatment of cells with 10 µM PTUPB for 5 hours followed by the addition of carboplatin did not alter the carboplatin induced DNA adduct formation (706 +/−26 adducts per $10^8$ nt with the carboplatin alone versus 606 +/−66 adducts per $10^8$ nt with the PTUPB pretreatment (p=0.071) (FIG. 10B). Clearly, PTUPB did not impact drug-target binding and metabolism of carboplatin in cell culture.

We next determined whether PTUPB affected the repair of carboplatin-DNA adducts since increased DNA repair is one of the major mechanisms of cellular resistance to platinum-based cancer therapy. To perform this experiment, 5637 cell cultures were treated with carboplatin alone or with PTUPB plus carboplatin combination for 4 hours followed by removal of both drugs, washing and additional culture with drug-free medium for 20 hours. At 24 hours, the platinum-DNA adduct levels were not significantly different in the two treatment groups, suggesting no difference of DNA repair between two treatments (104.1 +/−17.7 versus 90.8 +/−9.1 adducts/$10^8$ nt with the carboplatin alone or PTUPB plus carboplatin treatment (p=0.312)). The DNA repair rates were 21.2 +/−1.3 and 25.1 +/−8.1 adducts/$10^8$ nt per hour for the carboplatin alone and PTUPB plus carboplatin treatment groups (p=0.648), suggesting no difference of DNA repair between these two treatments.

Figure 10C:
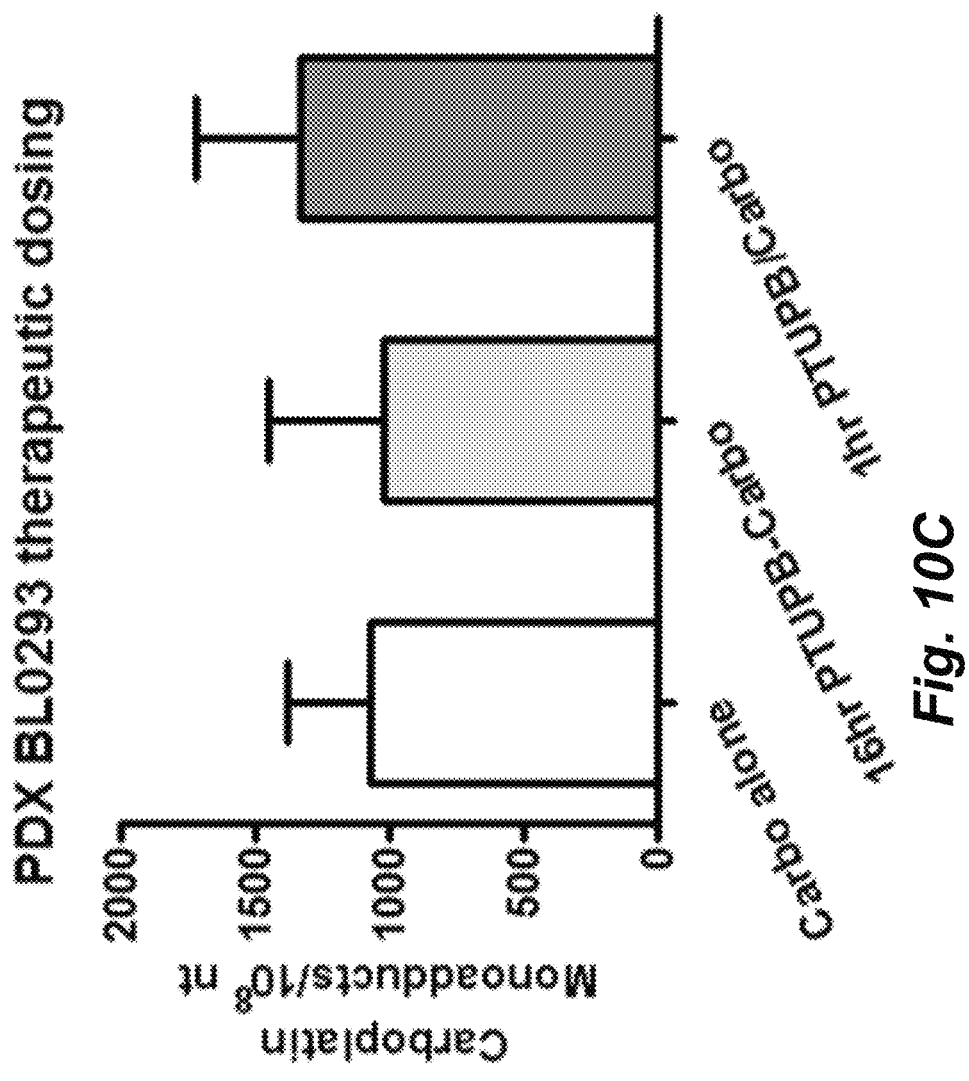

We also determined whether PTUPB influenced carboplatin-DNA adduct levels in vivo (FIG. 10C). PTUPB was administered either 16 hours or 1 hour before carboplatin injection and tumors were collected 24 hours after carboplatin treatment. Carboplatin-DNA adduct levels from isolated tumor DNA showed no significant difference between tumors that were treated with carboplatin alone, 16 hours of PTUPB (p=0.856) or 1 hour PTUPB (p=0.362) pre-treatment (1070±317 adducts/$10^8$ nt, 1019±434 adducts/$10^8$ nt, and 1334±384 adducts/$10^8$ nt, respectively). The in vivo data are fully consistent with the cell line data, and support PTUPB having a fully orthogonal mechanism of action compared to carboplatin and likely cisplatin.

PTUPB and the platinum drug cisplatin showed modest synergistic drug-drug interaction. Since we showed PTUPB potentiated the anti-tumor effect of cisplatin in vivo in bladder PDX models, we wanted to further study the mechanism of the combination effect of these two drugs in vitro. To address this question, the combination index (CI) method (27) was used to determine the drug-drug interaction of PTUPB and cisplatin. First, we determined the effect of single drug treatment on 5637 bladder cancer cells (FIG. 11A). Cultures of 5637 cells were treated with increasing concentrations of PTUPB or cisplatin (0, 0.01, 0.1, 1, 2, 5, 10, 20, 50, 100 µM). The IC50 of cisplatin and PTUPB on 5637 cells are 4.5 µM and 90.4 µM, respectively. Next, we determined the combination drug effect of PTUPB and cisplatin (FIG. 11B). 5637 cells were treated with different concentrations of cisplatin (0, 0.01 0.1, 0.5, 1, 2, 5, 10, 100 µM) in combination with different concentrations of PTUPB (1, 2, 5, 10 µM). The CI values of cisplatin and PTUPB were calculated indicating that PTUPB at concentrations of 1, 2, 5 and 10 µM showed modest synergistic effects in combination with cisplatin at 5 µM. In addition to the 5637 cell line, we also assessed the cytotoxicity of PTUPB and cisplatin in other human bladder cancer cell lines T24, J82, TCCSUP. A modest cisplatin potentiation was only observed in the 5637 cell line, but not in J82, T24 and TCCSUP cell lines (FIG. 12). Low or no direct effects on these cell lines is not surprising since we now know that the mechanism of action for PTUPB is predominantly anti-angiogenesis (20).

Figure 13A:
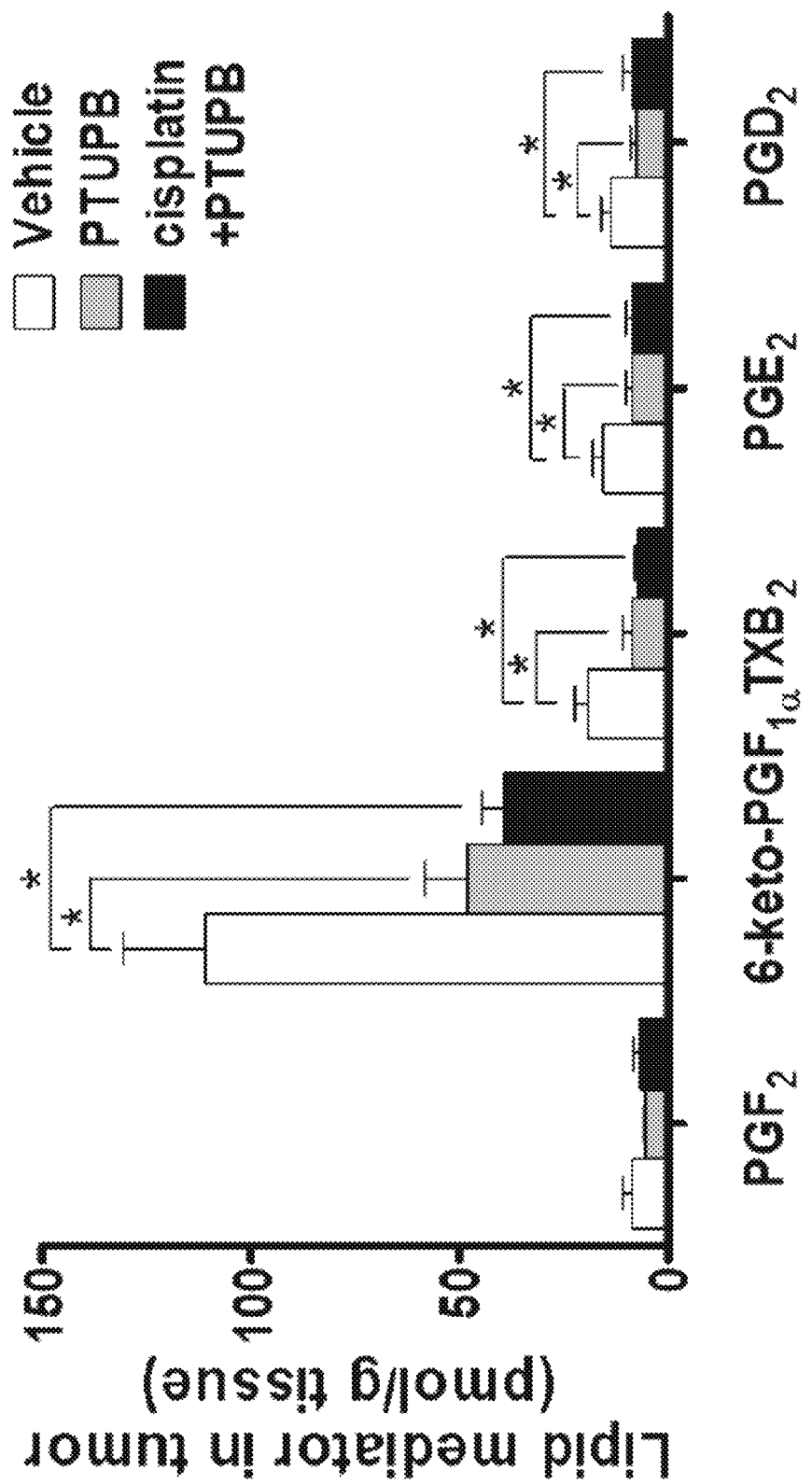
FIGS. 13A-B illustrate molecular correlative studies of PTUPB showing inhibition of both COX-2 and sEH pathways in tumor tissue. A, PTUPB reduces the levels of prostaglandins PGE2, PGD2, TXB2, 6-keto-PGF1α on COX-2 pathway. B, PTUPB increased levels of sEH substrates 10,11-EpDPE, 12,13-EpOME, 15,16-EpODE and decreased levels of sEH product 12,13-DiHOME on sEH pathway. The results are expressed as mean±SD. *P<0.05.
Figure 13B:
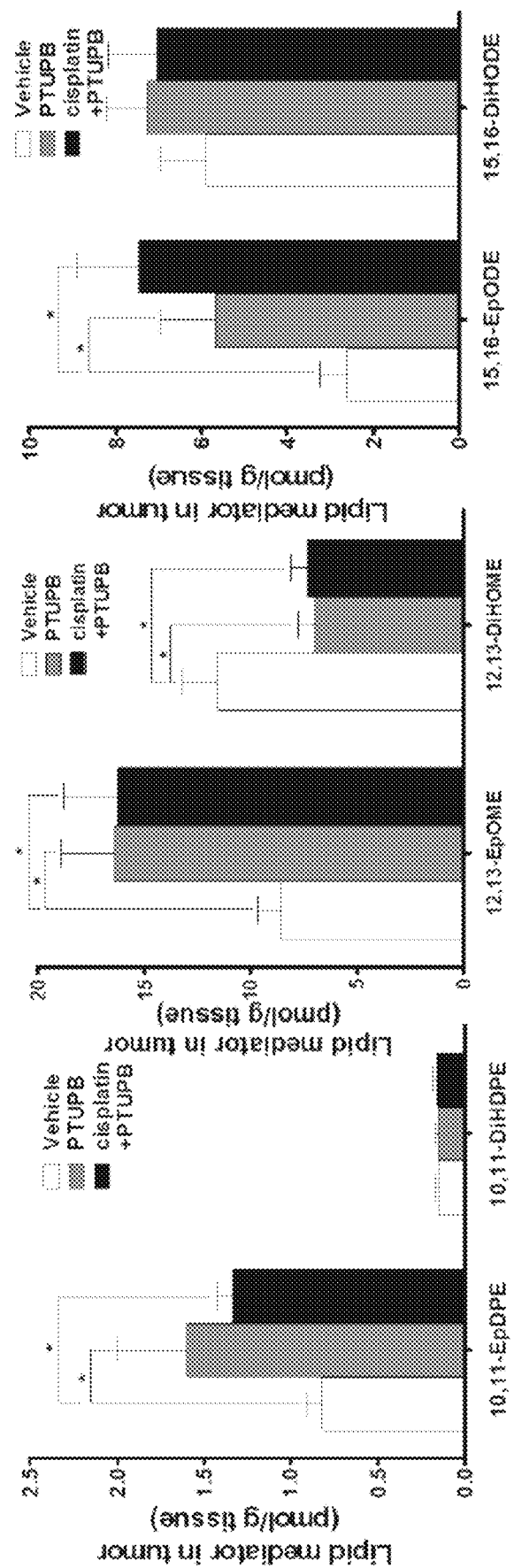
Figure 14A:
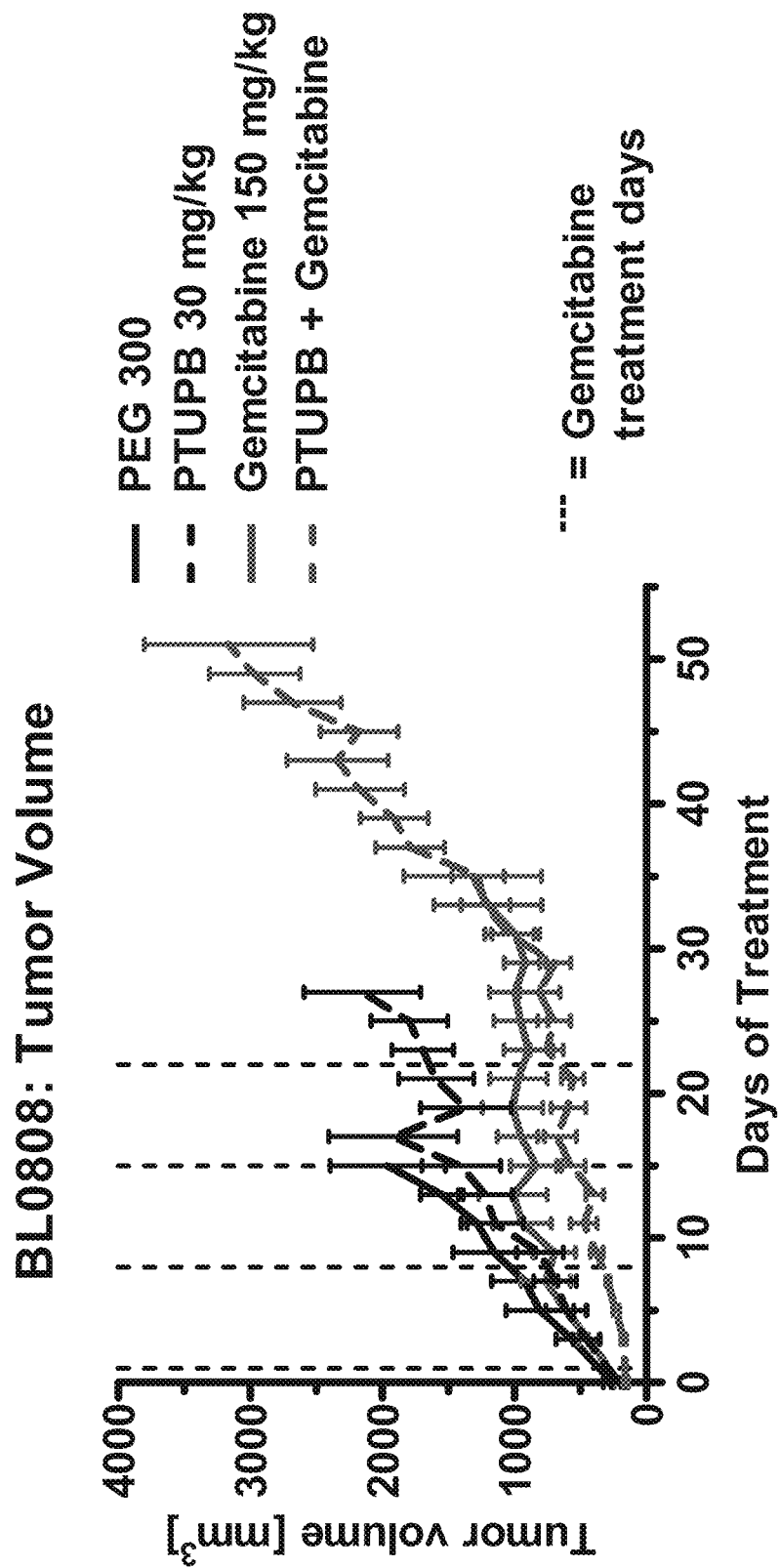
Figure 14C:
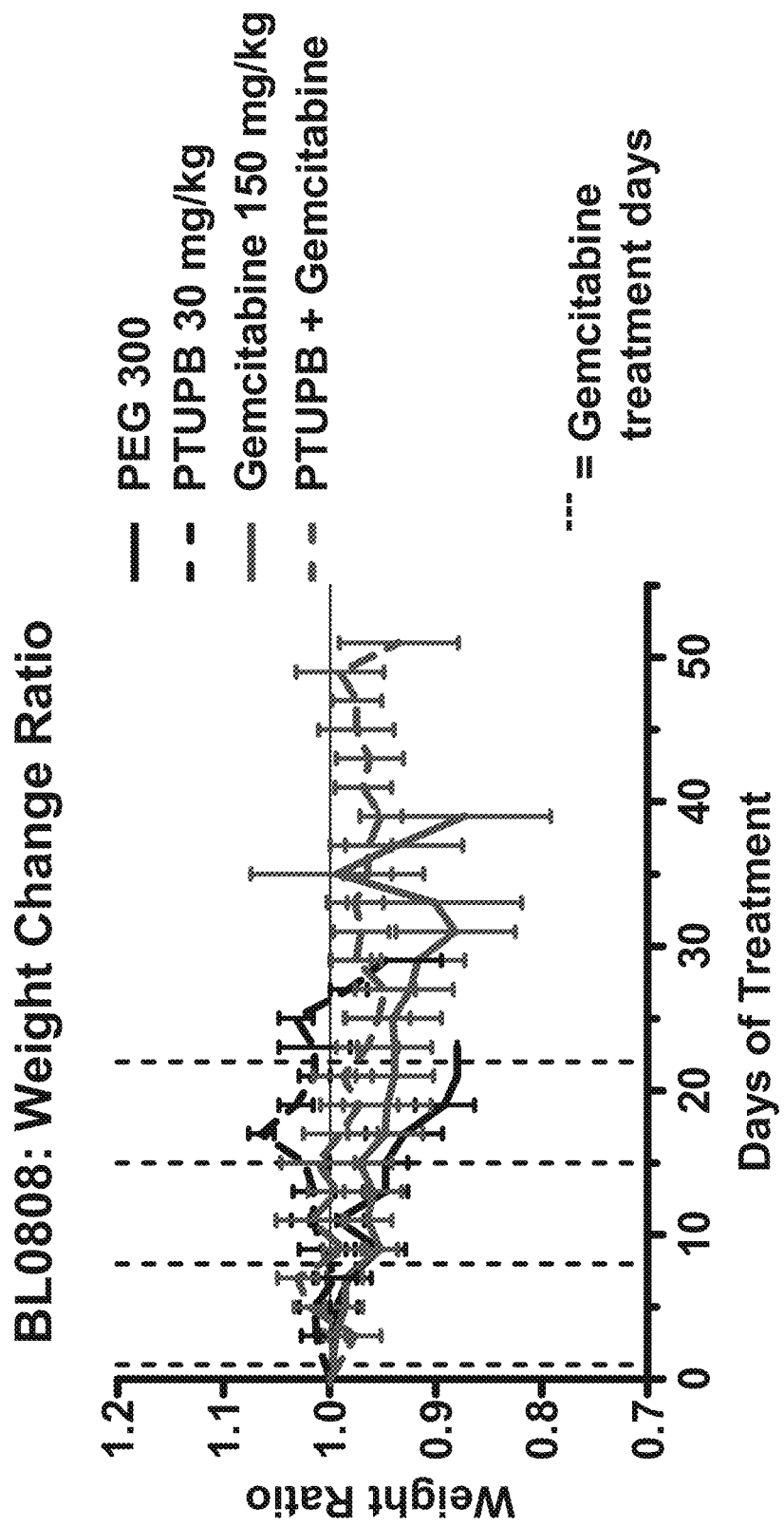

Molecular correlative studies of COX-2/sEH inhibitor PTUPB. To test whether PTUPB targets COX-2/sEH and show that inhibition of COX-2 and sEH pathways is involved in the mode of action of PTUPB in vivo, we analyzed oxylipin profiles using LC-tandem MS-based lipidomics (33). PTUPB treatment reduced the levels of COX-dependent prostaglandins PGE2, PGD2, TXB2, 6-keto-PGF1α in tumor by ~50% (p<0.05), indicating that PTUPB inhibited the COX-2 pathway in vivo (FIG. 13A). For the sEH dependent metabolites, PTUPB treatment caused an approximately two-fold increase of 12,13-EpOME, and about a 2-fold decrease on the corresponding diol metabolite 12,13-DiHOME. PTUPB also caused an approximately two-fold increase of 10,11-EpDPE, 15,16-EpODE in BL0269 tumors, whereas it had no effect on the corresponding diol metabolites 10,11-DiHDPE and 15,16-DiHODE (FIG. 13B). These results indicate that PTUPB inhibited both the COX-2 and sEH pathways in tumor tissue. The lipid mediators from other pathways were not significantly changed (Table 4). Together, these data support that PTUPB inhibits both COX-2 and sEH, although it may have effects on other cellular targets.

TABLE 4

LC-MS/MS Analysis of Lipid Metabolites in the Tumors of
PDX BL0269 Mice Treated with PTUPB and PTUPB + Cisplatin

| Group | Ctrl Mean ± SD | PTUPB Mean ± SD | p Value* | cisplatin + PTUPB Mean ± SD | p Value# |
|---|---|---|---|---|---|
| 6-keto-PGF1a | 110.87 ± 34.31 | 48.38 ± 19.83 | 0.0275 | 33.52 ± 13.22 | 0.0496 |
| TXB2 | 19.39 ± 9.28 | 8.85 ± 5.51 | 0.0135 | 7.23 ± 1.16 | 0.0042 |
| 9,12,13-TriHOME | 59.12 ± 34.77 | 74.52 ± 44.88 | 0.3452 | 55.50 ± 22.74 | 0.7906 |
| 9,10,13-TriHOME | 22.84 ± 13.29 | 27.61 ± 16.33 | 0.4293 | 18.27 ± 5.67 | 0.3085 |
| PGF2a | 8.70 ± 5.53 | 5.45 ± 1.27 | 0.1909 | 5.45 ± 1.27 | 0.2142 |
| PGE2 | 15.54 ± 7.13 | 8.66 ± 3.03 | 0.0685 | 8.88 ± 3.32 | 0.0414 |
| PGE1 | 0.71 ± 0.73 | 0.51 ± 0.36 | 0.3989 | 0.48 ± 0.18 | 0.2953 |
| PGD1 | 0.79 ± 0.62 | 0.89 ± 0.68 | 0.6963 | 0.82 ± 0.40 | 0.8926 |
| PGD2 | 13.98 ± 7.07 | 7.75 ± 2.60 | 0.1183 | 8.63 ± 5.55 | 0.1173 |
| 11,12-,15-TriHETrE | 89.00 ± 47.38 | 131.15 ± 94.58 | 0.1672 | 98.83 ± 56.01 | 0.7185 |
| PGJ2 | 1.01 ± 0.62 | 1.41 ± 1.54 | 0.3860 | 2.15 ± 0.52 | 0.0013 |
| 15,16-DiHODE | 5.90 ± 3.79 | 7.27 ± 3.02 | 0.3598 | 7.05 ± 3.34 | 0.5176 |
| 9,10-DiHODE | 0.21 ± 0.08 | 0.25 ± 0.16 | 0.3938 | 0.27 ± 0.12 | 0.2683 |
| 12,13-DiHODE | 0.45 ± 0.19 | 0.58 ± 0.30 | 0.2428 | 0.40 ± 0.11 | 0.4412 |
| 5,15-DiHETE | 0.78 ± 0.79 | 1.07 ± 1.45 | 0.5314 | 0.85 ± 0.78 | 0.8541 |
| 17,18-DiHETE | 1.25 ± 1.53 | 0.92 ± 0.43 | 0.4790 | 0.87 ± 0.31 | 0.4077 |
| LTB4 | 0.57 ± 0.73 | 0.56 ± 0.38 | 0.9920 | 0.53 ± 0.25 | 0.8670 |
| 12,13-DiHOME | 11.56 ± 4.95 | 6.95 ± 1.59 | 0.1026 | 7.30 ± 1.79 | 0.0407 |
| 9,10-DiHOME | 4.07 ± 7.80 | 2.96 ± 1.50 | 0.6312 | 2.68 ± 0.91 | 0.5377 |
| 19,20-DiHDPE | 5.74 ± 2.47 | 6.68 ± 2.82 | 0.3876 | 6.94 ± 2.03 | 0.2880 |
| 14,15-DiHETrE | 0.65 ± 0.42 | 0.74 ± 0.29 | 0.5396 | 0.86 ± 0.44 | 0.3693 |
| 16,17-DiHDPE | 0.37 ± 0.46 | 0.34 ± 0.14 | 0.8630 | 0.33 ± 0.11 | 0.7763 |
| 11,12-DiHETrE | 0.48 ± 0.29 | 0.38 ± 0.08 | 0.4868 | 0.33 ± 0.06 | 0.1262 |
| 13,14-DiHDPE | 0.17 ± 0.31 | 0.13 ± 0.05 | 0.6146 | 0.14 ± 0.04 | 0.6778 |
| 9-HOTrE | 1.14 ± 0.60 | 1.59 ± 1.07 | 0.1953 | 1.36 ± 0.58 | 0.4522 |
| 10,11-DiHDPE | 0.79 ± 2 | 0.15 ± 0.05 | 0.3638 | 0.17 ± 0.05 | 0.3730 |
| 8,9-DiHETrE | 0.80 ± 1.37 | 0.54 ± 0.24 | 0.5152 | 0.62 ± 0.19 | 0.6392 |
| EKODE | 10.74 ± 5.29 | 11.54 ± 4.44 | 0.6888 | 14.60 ± 7.72 | 0.3022 |
| 13-HOTrE | 10.93 ± 11.65 | 15.39 ± 13.59 | 0.3861 | 12.91 ± 7.93 | 0.6712 |
| 5,6-DiHETE | 0.15 ± 0.38 | 0.08 ± 0.05 | 0.5244 | 0.05 ± 0.01 | 0.3547 |
| 7,8-DiHDPE | 1.86 ± 5.41 | 0.50 ± 0.25 | 0.3946 | 0.52 ± 0.09 | 0.3902 |
| 20-HETE | 1.06 ± 0.59 | 1.57 ± 1.44 | 0.2551 | 1.41 ± 0.66 | 0.2939 |
| 15-HEPE | 12.81 ± 10.00 | 19.31 ± 18.28 | 0.2759 | 15.69 ± 10.65 | 0.5894 |
| 5,6-DiHETrE | 0.53 ± 0.60 | 0.46 ± 0.15 | 0.6944 | 0.50 ± 0.10 | 0.8686 |
| 4,5-DiHDPE | 0.15 ± 0.03 | 0.15 ± 0.04 | 0.8700 | 0.17 ± 0.06 | 0.6521 |
| 13-HODE | 528.15 ± 401.82 | 881.09 ± 695.68 | 0.1303 | 827.41 ± 507.95 | 0.2393 |
| 9-HODE | 95.99 ± 50.52 | 119.91 ± 64.13 | 0.3090 | 118.65 ± 50.93 | 0.3881 |
| 15(16)-EpODE | 2.61 ± 1.70 | 5.69 ± 3.58 | 0.0455 | 7.48 ± 2.85 | 0.0336 |
| 15-HETE | 564.29 ± 390.44 | 883.22 ± 745.85 | 0.1885 | 763.30 ± 477.81 | 0.3977 |
| 17-HDoHE | 648.32 ± 482.38 | 1,094.62 ± 1,118.63 | 0.2018 | 942.40 ± 643.84 | 0.3490 |
| 11-HETE | 38.68 ± 15.96 | 46.51 ± 32.84 | 0.4504 | 40.17 ± 10.46 | 0.8114 |
| 12(13)-EpODE | 0.61 ± 0.16 | 0.71 ± 0.57 | 0.6431 | 0.75 ± 0.34 | 0.4914 |
| 15-oxo-ETE | 16.96 ± 16.97 | 28.44 ± 29.12 | 0.2362 | 8.44 ± 4.79 | 0.1149 |
| 9-oxo-ODE | 29.92 ± 15.69 | 29.87 ± 12.67 | 0.9926 | 23.63 ± 4.73 | 0.2051 |
| 8-HETE | 9.44 ± 4.11 | 13.20 ± 10.08 | 0.2266 | 11.68 ± 4.50 | 0.3268 |
| 12-HETE | 934.05 ± 552.19 | 1,166.14 ± 794.19 | 0.4018 | 1,179.28 ± 402.75 | 0.2945 |
| 11(12)-EpETE | 5.26 ± 2.49 | 5.57 ± 4.17 | 0.8218 | 7.09 ± 3.31 | 0.2650 |
| 15(S)-HETrE | 118.21 ± 90.90 | 231.14 ± 210.19 | 0.0902 | 183.68 ± 125.41 | 0.2864 |
| 12-oxo-ETE | 185.01 ± 158.00 | 180.98 ± 135.18 | 0.9462 | 84.58 ± 45.57 | 0.0515 |
| 5-HETE | 6.79 ± 2.95 | 8.22 ± 5.32 | 0.4093 | 6.07 ± 1.26 | 0.4643 |
| 19(20)-EpDPE | 3.12 ± 3.89 | 2.64 ± 1.15 | 0.6879 | 3.00 ± 1.18 | 0.9223 |
| 12(13)-EpOME | 8.55 ± 2.70 | 16.43 ± 7.05 | 0.0242 | 16.28 ± 5.55 | 0.0319 |
| 14(15)-EpETrE | 3.12 ± 1.23 | 3.86 ± 1.59 | 0.3505 | 3.90 ± 0.72 | 0.2293 |
| 9(10)-EpOME | 10.92 ± 6.54 | 12.24 ± 4.86 | 0.5732 | 11.94 ± 5.42 | 0.7259 |
| 10(11)-EpDPE | 0.82 ± 0.19 | 1.60 ± 0.91 | 0.0971 | 1.33 ± 0.15 | 0.0079 |
| 11(12)-EpETrE | 3.69 ± 1.10 | 7.01 ± 2.76 | 0.0233 | 5.10 ± 0.49 | 0.0322 |
| 8(9)-EpETrE alt | 7.14 ± 15.88 | 3.02 ± 1.72 | 0.3814 | 2.63 ± 1.23 | 0.3287 |
| 5(6)-EpETrE | 197.08 ± 75.62 | 182.39 ± 133.11 | 0.7349 | 142.51 ± 69.11 | 0.1497 |

Discussion

As a dual inhibitor of COX-2 and sEH, PTUPB potentiated the anti-tumor activity of cisplatin without increasing the toxicity in mice bearing bladder cancer PDXs. We also performed experiments to examine the efficacy of combination treatments of celecoxib plus cisplatin or t-AUCB plus cisplatin in a bladder PDX model. We did not observe any potentiation of cisplatin by celecoxib with respect to inhibiting tumor growth. It was reported by Kurtova et al that blocking tumor expression of PGE2 with celecoxib modulates tumor repopulation after several cycles and abrogates bladder cancer chemoresistance (34). However, these results are not contradictory with our studies. Kurtova et al used a single PDX from a GC resistant subject (which was paradoxically quite responsive to GC in the mouse); and a different dosing regimen showing that celecoxib did not have a pronounced effect on GC response in their PDX model until the fourth cycle of GC treatment. Our protocol only had two cycles of GC, and was not designed to assess long-term tumor repopulation by cancer stem cells.

We not only showed that PTUPB enhanced cisplatin and GC efficacy, but also began to define the underlying mechanisms of potentiation. The increased efficacy was not due to increased PTUPB-DNA adduct formation. We gathered evidence that the potentiation is possibly due to in vivo factors, such as angiogenesis, and reduced activation of proliferation signaling including the AKT and ERK signaling pathways. Treatment with cisplatin and PTUPB in vivo decreased the levels of both p-ERK and p-AKT in tumor tissues, suggesting that these two major signaling pathways were down regulated. We previously reported the evidence of anti-angiogenic properties of PTUPB (20).

PTUPB has the potential for improving platinum-based chemotherapy in the clinic. Even though targeted therapy and immunotherapy have emerged as promising therapeutic modalities, cytotoxic chemotherapy will still be the mainstay in the foreseeable future. For example, targeted and immunotherapies currently benefit only a minority of subjects with non-small cell lung and bladder cancers. The response rate of immunotherapy in both cancers is approximately 20 percent or less (35, 36).

In conclusion, the COX2/sEH dual inhibitor PTUPB potentiates cisplatin and GC, possibly synergistically, in bladder cancer PDXs in vivo without increasing toxicity. PTUPB and cisplatin treatment increases apoptosis and decreases the activity of the AKT and ERK pathways, but does not increase the formation of platinum-DNA adducts, the most critical step of platinum-induced cell death.

REFERENCES

1. Ho G Y, Woodward N, Coward J I. Cisplatin versus carboplatin: comparative review of therapeutic management in solid malignancies. Critical reviews in oncology/hematology. 2016;102:37-46.
2. Kamat A M, Hahn N M, Efstathiou J A, Lerner S P, Malmstrom P U, Choi W, et al. Bladder cancer. Lancet. 2016.
3. Grivas P D, Day K C, Karatsinides A, Paul A, Shakir N, Owainati I, et al. Evaluation of the antitumor activity of dacomitinib in models of human bladder cancer. Molecular medicine. 2013;19:367-76.
4. Xu L, Stevens J, Hilton M B, Seaman S, Conrads T P, Veenstra T D, et al. COX-2 inhibition potentiates antiangiogenic cancer therapy and prevents metastasis in preclinical models. Science translational medicine. 2014;6:242ra84.
5. Morisseau C, Hammock B D. Impact of soluble epoxide hydrolase and epoxyeicosanoids on human health. Annual review of pharmacology and toxicology. 2013;53:37-58.
6. Spector A A, Norris A W. Action of epoxyeicosatrienoic acids on cellular function. American journal of physiology Cell physiology. 2007;292:C996-1012.
7. Inceoglu B, Jinks S L, Ulu A, Hegedus C M, Georgi K, Schmelzer K R, et al. Soluble epoxide hydrolase and epoxyeicosatrienoic acids modulate two distinct analgesic pathways. Proceedings of the National Academy of Sciences of the United States of America. 2008;105:18901-6.
8. Shen H C, Hammock B D. Discovery of inhibitors of soluble epoxide hydrolase: a target with multiple potential therapeutic indications. Journal of medicinal chemistry. 2012;55:1789-808.
9. Spector A A, Fang X, Snyder G D, Weintraub N L. Epoxyeicosatrienoic acids (EETs): metabolism and biochemical function. Progress in lipid research. 2004;43:55-90.
10. Chen D, Whitcomb R, MacIntyre E, Tran V, Do Z N, Sabry J, et al. Pharmacokinetics and pharmacodynamics of AR9281, an inhibitor of soluble epoxide hydrolase, in single- and multiple-dose studies in healthy human subjects. Journal of clinical pharmacology. 2012;52:319-28.
11. Lazaar A L, Yang L, Boardley R L, Goyal N S, Robertson J, Baldwin S J, et al. Pharmacokinetics, pharmacodynamics and adverse event profile of GSK2256294, a novel soluble epoxide hydrolase inhibitor. British journal of clinical pharmacology. 2016;81:971-9.
12. Schmelzer K R, Kubala L, Newman J W, Kim I H, Eiserich J P, Hammock B D. Soluble epoxide hydrolase is a therapeutic target for acute inflammation. Proceedings of the National Academy of Sciences of the United States of America. 2005;102:9772-7.
13. Ghosh N, Chaki R, Mandal V, Mandal S C. COX-2 as a target for cancer chemotherapy. Pharmacological reports: PR. 2010;62:233-44.
14. Gridelli C, Gallo C, Ceribelli A, Gebbia V, Gamucci T, Ciardiello F, et al. Factorial phase III randomised trial of rofecoxib and prolonged constant infusion of gemcitabine in advanced non-small-cell lung cancer: the GEmcitabine-COxib in NSCLC (GECO) study. The Lancet Oncology. 2007;8:500-12.
15. Groen H J, Sietsma H, Vincent A, Hochstenbag M M, van Putten J W, van den Berg A, et al. Randomized, placebo-controlled phase III study of docetaxel plus carboplatin with celecoxib and cyclooxygenase-2 expression as a biomarker for subjects with advanced non-small-cell lung cancer: the NVALT-4 study. Journal of clinical oncology: official journal of the American Society of Clinical Oncology. 2011;29:4320-6.
16. Pan C X, Loehrer P, Seitz D, Helft P, Juliar B, Ansari R, et al. A phase II trial of irinotecan, 5-fluorouracil and leucovorin combined with celecoxib and glutamine as first-line therapy for advanced colorectal cancer. Oncology. 2005; 69:63-70.
17. Schmelzer K R, Inceoglu B, Kubala L, Kim I H, Jinks S L, Eiserich J P, et al. Enhancement of antinociception by coadministration of nonsteroidal anti-inflammatory drugs and soluble epoxide hydrolase inhibitors. Proceedings of the National Academy of Sciences of the United States of America. 2006;103:13646-51.
18. Wagner K, Inceoglu B, Hammock B D. Soluble epoxide hydrolase inhibition, epoxygenated fatty acids and nociception. Prostaglandins & other lipid mediators. 2011; 96:76-83.
19. Goswami S K, Wan D, Yang J, Trindade da Silva C A, Morisseau C, Kodani S D, et al. Anti-Ulcer Efficacy of Soluble Epoxide Hydrolase Inhibitor TPPU on Diclofenac-Induced Intestinal Ulcers. The Journal of pharmacology and experimental therapeutics. 2016;357:529-36.
20. Zhang G, Panigrahy D, Hwang S H, Yang J, Mahakian L M, Wettersten H I, et al. Dual inhibition of cyclooxygenase-2 and soluble epoxide hydrolase synergistically suppresses primary tumor growth and metastasis. Proceedings of the National Academy of Sciences of the United States of America. 2014;111:11127-32.
21. Hwang S H, Wagner K M, Morisseau C, Liu J Y, Dong H, Wecksler A T, et al. Synthesis and structure-activity relationship studies of urea-containing pyrazoles as dual inhibitors of cyclooxygenase-2 and soluble epoxide hydrolase. Journal of medicinal chemistry. 2011;54:3037-50.

22. Pan C X, Zhang H, Tepper C G, Lin T Y, Davis R R, Keck J, et al. Development and Characterization of Bladder Cancer Subject-derived Xenografts for Molecularly Guided Targeted Therapy. PloS one. 2015;10:e0134346.

23. Zimmermann M, Wang S S, Zhang H, Lin T Y, Malfatti M, Haack K, et al. Microdose-Induced Drug-DNA Adducts as Biomarkers of Chemotherapy Resistance in Humans and Mice. Mol Cancer Ther. 2017;16:376-87.

24. Hwang S H, Tsai H J, Liu J Y, Morisseau C, Hammock B D. Orally bioavailable potent soluble epoxide hydrolase inhibitors. Journal of medicinal chemistry. 2007;50:3825-40.

25. Ognibene T J, Bench G, Vogel J S, Peaslee G F, Murov S. A high-throughput method for the conversion of CO2 obtained from biochemical samples to graphite in septa-sealed vials for quantification of 14C via accelerator mass spectrometry. Analytical chemistry. 2003;75:2192-6.

26. Chou T C. Theoretical basis, experimental design, and computerized simulation of synergism and antagonism in drug combination studies. Pharmacological reviews. 2006; 58:621-81.

27. Chou T C. Drug combination studies and their synergy quantification using the Chou-Talalay method. Cancer research. 2010;70:440-6.

28. Sebaugh J L. Guidelines for accurate EC50/IC50 estimation. Pharm Stat. 2011;10:128-34.

29. Liu J Y, Yang J, Inceoglu B, Qiu H, Ulu A, Hwang S H, et al. Inhibition of soluble epoxide hydrolase enhances the anti-inflammatory effects of aspirin and 5-lipoxygenase activation protein inhibitor in a murine model. Biochem Pharmacol. 2010;79:880-7.

30. Henderson P T, Li T, He M, Zhang H, Malfatti M, Gandara D, et al. A microdosing approach for characterizing formation and repair of carboplatin-DNA monoadducts and chemoresistance. International journal of cancer. 2011;129: 1425-34.

31. Henderson P T, Pan C X. Human microdosing for the prediction of subject response. Bioanalysis. 2010;2:373-6.

32. Wang S, Zhang H, Scharadin T M, Zimmermann M, Hu B, Pan A W, et al. Molecular Dissection of Induced Platinum Resistance through Functional and Gene Expression Analysis in a Cell Culture Model of Bladder Cancer. PloS one. 2016;11:e0146256.

33. Thalji R K, McAtee J J, Belyanskaya S, Brandt M, Brown G D, Costell M H, et al. Discovery of 1-(1,3,5-triazin-2-yl)piperidine-4-carboxamides as inhibitors of soluble epoxide hydrolase. Bioorg Med Chem Lett. 2013; 23:3584-8.

34. Kurtova A V, Xiao J, Mo Q, Pazhanisamy S, Krasnow R, Lerner S P, et al. Blocking PGE2-induced tumour repopulation abrogates bladder cancer chemoresistance. Nature. 2015;517:209-13.

35. Powles T, Eder J P, Fine G D, Braiteh F S, Loriot Y, Cruz C, et al. MPDL3280A (anti-PD-L1) treatment leads to clinical activity in metastatic bladder cancer. Nature. 2014; 515:558-62.

36. Borghaei H, Paz-Ares L, Horn L, Spigel D R, Steins M, Ready N E, et al. Nivolumab versus Docetaxel in Advanced Nonsquamous Non-Small-Cell Lung Cancer. The New England journal of medicine. 2015;373:1627-39.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of prolonging survival in a subject in need of cancer treatment comprising: administering to the subject a regimen of one or more chemotherapeutic agents, an inhibitor of soluble epoxide hydrolase (sEHi) and a non-steroidal anti-inflammatory drug (NSAID), wherein the NSAID inhibits one or more enzymes selected from the group consisting of cyclo-oxygenase ("COX")-1, COX-2, and 5-lipoxygenase ("5-LOX"), wherein
the one or more chemotherapeutic agents is selected from the group consisting of a platinum coordination complex and a nucleoside analog.

2. A method of reducing or inhibiting tumor growth in a subject in need of cancer treatment comprising: administering to the subject a regimen of one or more chemotherapeutic agents, an inhibitor of soluble epoxide hydrolase (sEHi) and a non-steroidal anti-inflammatory drug (NSAID), wherein the NSAID inhibits one or more enzymes selected from the group consisting of cyclo-oxygenase ("COX")-1, COX-2, and 5-lipoxygenase ("5-LOX"), wherein
the one or more chemotherapeutic agents is selected from the group consisting of a platinum coordination complex and a nucleoside analog.

3. The method of claim 2, wherein tumor growth is reduced or inhibited to a greater amount or at a greater rate with the regimen as compared with administering only the one or more chemotherapeutic agents.

4. The method of claim 2, wherein the survival of the subject is prolonged with the regimen as compared with administering only the one or more chemotherapeutic agents.

5. The method of claim 2, wherein the subject receives a first treatment regimen of one or more chemotherapeutic agents, and subsequently the subject receives a second treatment regimen comprising the one or more chemotherapeutic agents, the sEHi and the NSAID.

6. The method of claim 1, wherein the platinum coordination complex is selected from the group consisting of cisplatin, carboplatin, oxaliplatin, nedaplatin, saraplatin, lobaplatin, heptaplatin, and mixtures thereof.

7. The method of claim 2, wherein the platinum coordination complex is selected from the group consisting of cisplatin, carboplatin, oxaliplatin, nedaplatin, saraplatin, lobaplatin, heptaplatin, and mixtures thereof.

8. The method of claim 1, wherein the nucleoside analog is selected from the group consisting of gemcitabine, cytarabine, capecitabine, 5-fluorouracil, 5 fluorodeoxyuridine, 5-fluorodeoxyuridine monophosphate, 5-azacytidine, and mixtures thereof.

9. The method of claim 2, wherein the nucleoside analog is a pyrimidine analog.

10. The method of claim 9, wherein the pyrimidine analog is selected from the group consisting of gemcitabine, cytarabine , capecitabine, 5-fluorouracil, 5-fluorodeoxyuridine, 5-fluorodeoxyuridine monophosphate, 5-azacytidine, and mixtures thereof.

11. The method of claim 2, wherein the inhibitor of a cyclo-oxygenase is a preferential or selective inhibitor of COX-2.

12. The method of claim 11, wherein the preferential or selective inhibitor of COX-2 is selected from the group consisting of celecoxib, valdecoxib, lumiracoxib, etoricoxib, parecoxib, rofecoxib, nabumetone, meloxicam, and mixtures thereof.

13. The method of claim 2, wherein the NSAID is selected from the group consisting of aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, sodium salicylate, alkyl salicylate and disalicylate.

14. The method of claim 2, wherein the inhibitor of sEH and the NSAID are administered via the same route of administration.

15. The method of claim 14, comprising administering to the subject a dual inhibitor of sEH and COX-2.

16. The method of claim 15, wherein the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB).

17. The method of claim 15, wherein the dual inhibitor of sEH and COX-2 is a compound selected from the group consisting of 1-Adamantan-1-yl-3-[1-(4-methanesulfonyl-phenyl)-5-phenyl-1H-pyrazol-3-ylmethyl]-urea (compound 1860), 1-Cycloheptyl-3-[1-(4-methanesulfonyl-phenyl)-5-phenyl-1H-pyrazol-3-ylmethyl]-urea (compound 2321), 1-[1-(4-Methanesulfonyl-phenyl)-5-phenyl-1H-pyrazol-3-ylmethyl]-3-phenyl-urea) (compound 2322), (1-[1-(4-Methanesulfonyl-phenyl)-5-phenyl-1H-pyrazol-3-ylmethyl]-3-(4-trifluoromethoxy-phenyl)-urea (compound 2323), 1-[1-(4-Methanesulfonyl-phenyl)-5-phenyl-1H-pyrazol-3-ylmethyl]-3-(4-trifluoromethyl-phenyl)-urea (compound 2324), 1-[1-(4-Methanesulfonyl-phenyl)-5-phenyl-1H-pyrazol-3-ylmethyl]-3-(3-trifluoromethyl-phenyl)-urea (compound 1861), 4-{5-Phenyl-3-[3-(3-trifluoromethyl-phenyl)-ureidomethyl]-pyrazol-1-yl}-benzenesulfonamide (compound 2107), 1-[5-tert-Butyl-1-(4-methanesulfonyl-phenyl)-1H-pyrazol-3-ylmethyl]-3-(3-trifluoromethyl-phenyl)-urea (compound 2106), 4-{5-Phenyl-3-[3-(3-trifluoromethyl-phenyl)-ureido]-pyrazol-1-yl}-benzenesulfonamide (compound 2121), 4-(5-Phenyl-3-{2-[3-(3-trifluoromethyl-phenyl)-ureido]-ethyl}-pyrazol-1-yl)-benzenesulfonamide (compound 2313), 1-{3-[1-(4-Methanesulfonyl-phenyl)-5-phenyl-1H-pyrazol-3-yl]-propyl}-3-(3-trifluoromethyl-phenyl)-urea (compound 1862), 4-(5-Phenyl-3-{3-[3-(3-trifluoromethyl-phenyl)-ureido]-propyl}-pyrazol-1-yl)-benzenesulfonamide (compound 2246), 4-(5-p-Tolyl-3-{3-[3-(3-trifluoromethyl-phenyl)-ureido]-propyl}-pyrazol-1-yl)-benzenesulfonamide (compound 2152), 4-(3-{3-[3-(2,6-Diisopropyl-phenyl)-ureido]-propyl}-5-phenyl-pyrazol-1-yl)-benzenesulfonamide (compound 2325), 4-{5-Phenyl-3-[3-(3-phenyl-ureido)-propyl]-pyrazol-1-yl}-benzenesulfonamide (compound 2245), 4-{3-[3-(3-Adamantan-1-yl-ureido)-propyl]-5-phenyl-pyrazol-1-yl}-benzenesulfonamide (compound 2326), 4-{3-[3-(3-Cycloheptyl-ureido)-propyl]-5-phenyl-pyrazol-1-yl}-benzenesulfonamide (compound 2247), 4-(3-{3-[3-(4-Chloro-phenyl)-ureido]-propyl}-5-phenyl-pyrazol-1-yl)-benzenesulfonamide (compound 2327), 4-(5-Phenyl-3-{3-[3-(4-trifluoromethyl-phenyl)-ureido]-propyl}-pyrazol-1-yl)-benzenesulfonamide (compound 2328) and 4-(5-Phenyl-3-{3-[3-(4-trifluoromethoxy-phenyl)-ureido]-propyl}-pyrazol-1-yl)-benzenesulfonamide (compound 2329).

18. The method of claim 2, wherein the subject has a cancer selected from the group consisting of: bladder, ovarian, cervical, breast, testicular, prostate, head and neck, oral, esophageal, gastric, lung, pancreatic, skin, leukemia, colon and colorectal.

19. The method of claim 16, wherein the platinum coordination complex is selected from the group consisting of cisplatin, carboplatin, oxaliplatin, nedaplatin, saraplatin, lobaplatin, heptaplatin, and mixtures thereof.

20. The method of claim 16, wherein the nucleoside analog is selected from the group consisting of gemcitabine, cytarabine, capecitabine, 5-fluorouracil, 5-fluorodeoxyuridine, 5-fluorodeoxyuridine monophosphate, 5-azacytidine, and mixtures thereof.

21. The method of claim 2, wherein reduction or inhibition of tumor growth in a subject blocks or inhibits metastasis.

* * * * *